[12] United States Patent
Pomero et al.

(10) Patent No.: US 11,007,019 B2
(45) Date of Patent: May 18, 2021

(54) SURGICAL ORIENTATION SYSTEM USING BONE GEOMETRY FOR REPEATABLE POSITIONING

(71) Applicant: PYTHEAS NAVIGATION, Marseilles (FR)

(72) Inventors: Vincent Pomero, Gardanne (FR); Yann Glard, Marseilles (FR)

(73) Assignee: PYTHEAS NAVIGATION, Marseilles (FR)

( * ) Notice: Subject to any disclaimer, the term of this patent is extended or adjusted under 35 U.S.C. 154(b) by 101 days.

(21) Appl. No.: 16/486,878

(22) PCT Filed: Feb. 20, 2018

(86) PCT No.: PCT/FR2018/050390
§ 371 (c)(1),
(2) Date: Aug. 19, 2019

(87) PCT Pub. No.: WO2018/150151
PCT Pub. Date: Aug. 23, 2018

(65) Prior Publication Data
US 2020/0008882 A1   Jan. 9, 2020

(30) Foreign Application Priority Data
Feb. 20, 2017   (FR) ...................................... 17 51334

(51) Int. Cl.
*G06K 9/00* (2006.01)
*A61B 34/20* (2016.01)
(Continued)

(52) U.S. Cl.
CPC .............. *A61B 34/20* (2016.02); *A61B 90/39* (2016.02); *G06T 7/74* (2017.01);
(Continued)

(58) Field of Classification Search
None
See application file for complete search history.

(56) References Cited

U.S. PATENT DOCUMENTS 5,115,708 A * 5/1992 Spariat .................. B64G 1/641
102/378
5,676,673 A   10/1997 Ferre et al.
(Continued)

FOREIGN PATENT DOCUMENTS

| EP | 1088525 A1 | 4/2001 |
| FR | 3030222 A1 | 6/2016 |
| GB | 2382777 A | 6/2003 |

OTHER PUBLICATIONS

International Search Report, dated May 22, 2018, from corresponding PCT application No. PCT/FR2018/050390.

*Primary Examiner* — Shervin K Nakhjavan
(74) *Attorney, Agent, or Firm* — Nixon & Vanderhye

(57) ABSTRACT

Disclosed is a surgical ancillary device, preferably Y-shaped, including three contact portions intended to come into contact with three corresponding reference areas of an operation area, and a unit for determining an orientation coordinate system of the ancillary device in a Galilean orientation coordinate system. At least one of the first and second contact portions, and preferably both, includes a concave or convex end, for example a roller that is optionally mounted so as to be rotatably movable, or a gutter-shaped element. Each end comes into contact with two reference points in the corresponding reference area, which is respectively convex or concave. These two points accurately guide the rotation of the ancillary device in order to bring the third contact portion into contact with the third reference area. The orientations of the ancillary device define the orientation coordinate system, the determination of which can therefore be accurately reproduced.

20 Claims, 11 Drawing Sheets

(51) Int. Cl.
  *A61B 90/00* (2016.01)
  *G06T 7/73* (2017.01)
(52) U.S. Cl.
  CPC .............. *A61B 2034/2048* (2016.02); *A61B 2034/2055* (2016.02); *A61B 2034/2065* (2016.02); *A61B 2034/2068* (2016.02); *A61B 2090/3916* (2016.02); *A61B 2090/3983* (2016.02); *G06T 2207/10028* (2013.01)

(56) References Cited

U.S. PATENT DOCUMENTS

| | | | |
|---|---|---|---|
| 2004/0134341 A1* | 7/2004 | Sandoz | F41G 3/02 |
| | | | 89/41.09 |
| 2011/0257653 A1 | 10/2011 | Hughes et al. | |
| 2015/0018622 A1* | 1/2015 | Tesar | A61B 50/13 |
| | | | 600/202 |
| 2016/0100773 A1 | 4/2016 | Ching et al. | |
| 2017/0354426 A1* | 12/2017 | Glard | A61B 34/20 |

* cited by examiner

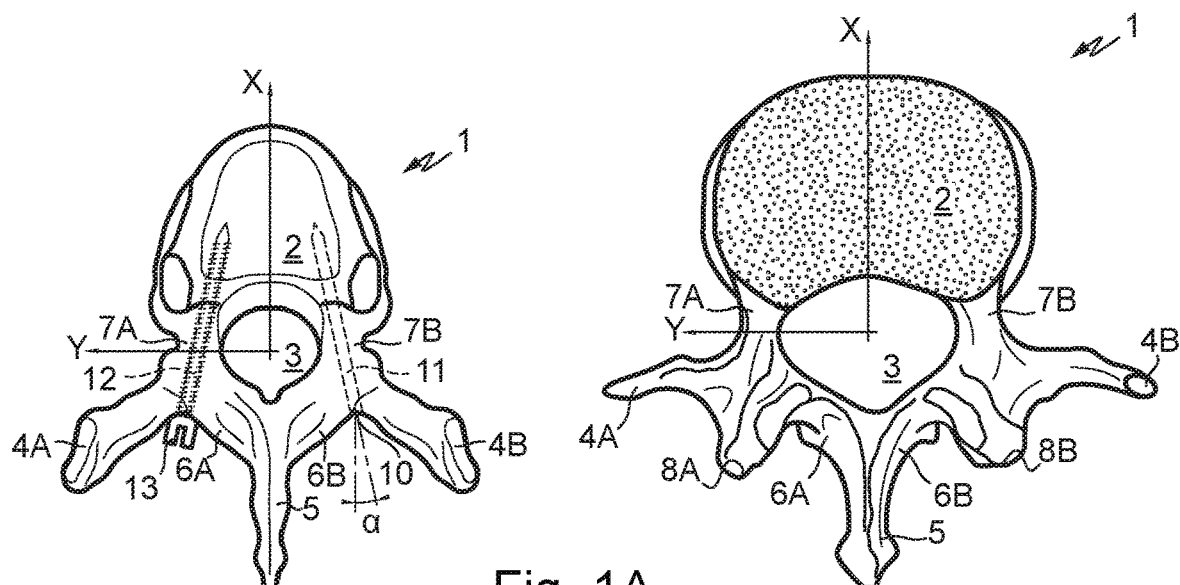
Fig. 1A
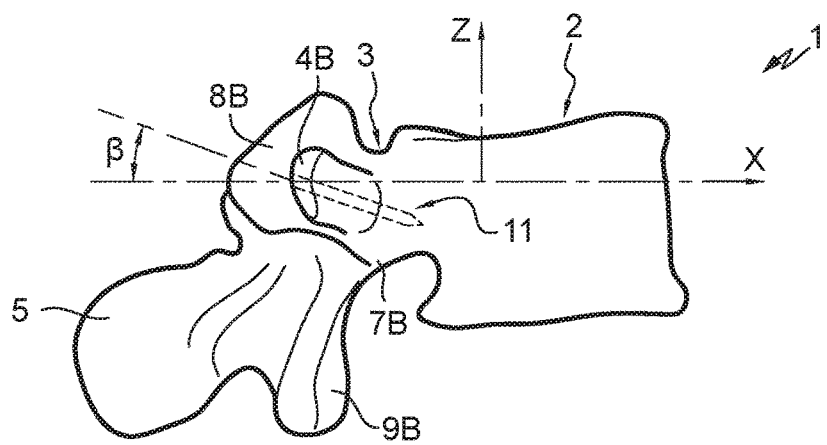
Fig. 1B
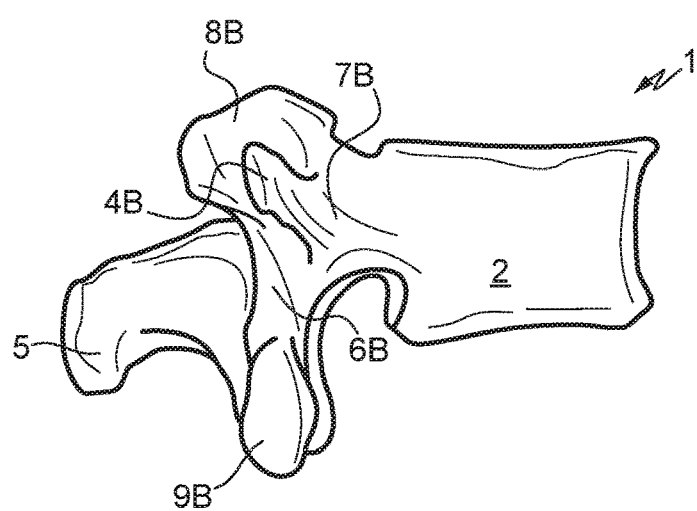

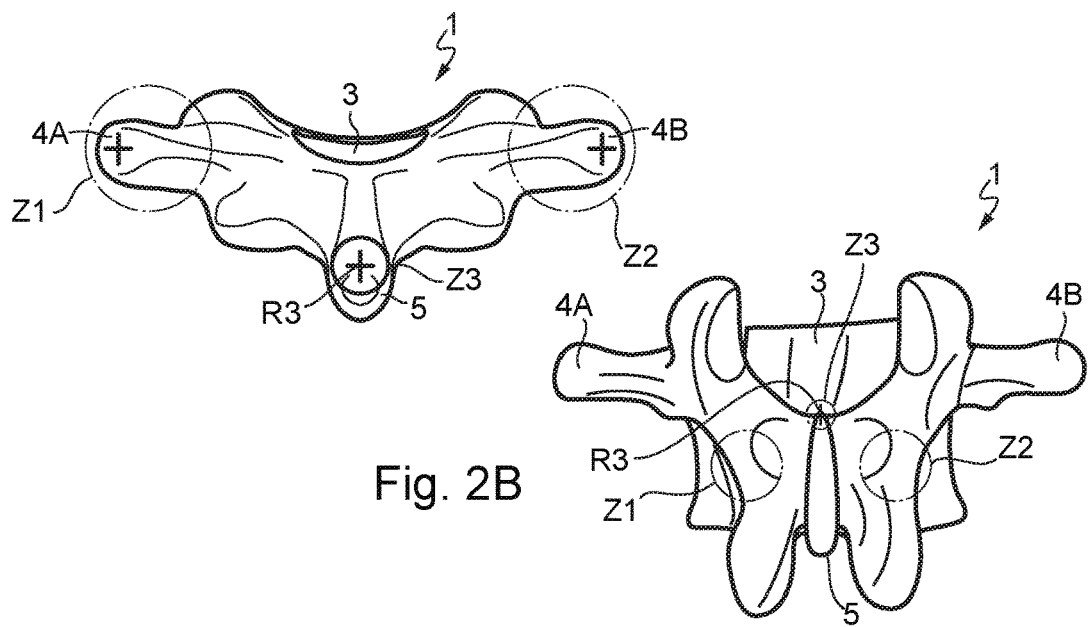
Fig. 2B
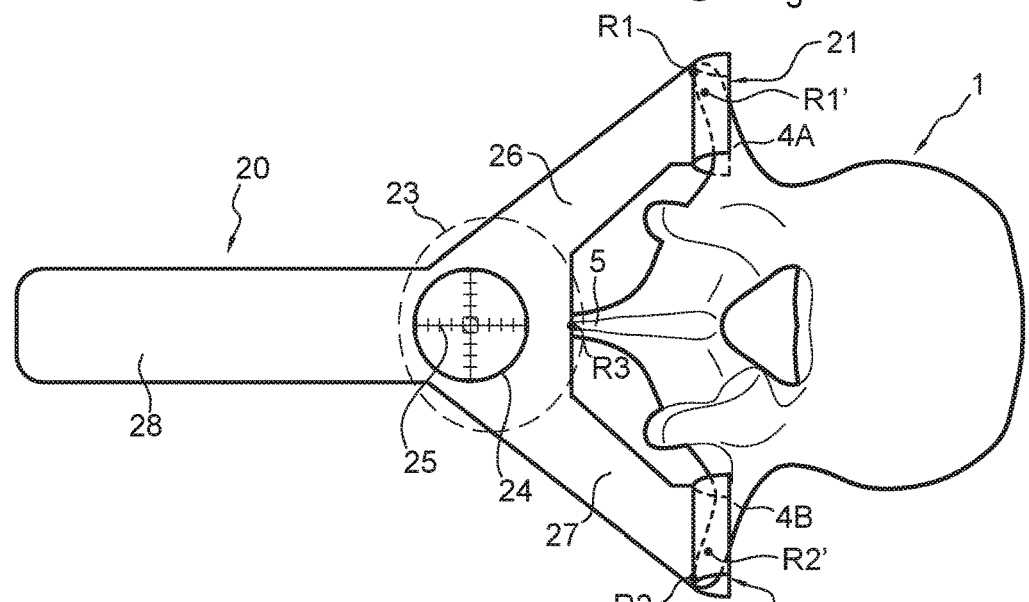
Fig. 3A
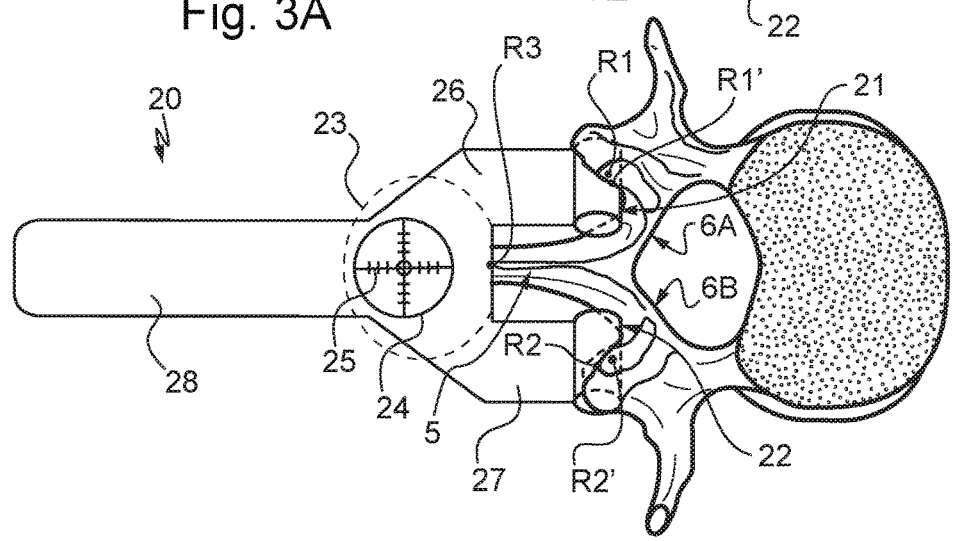

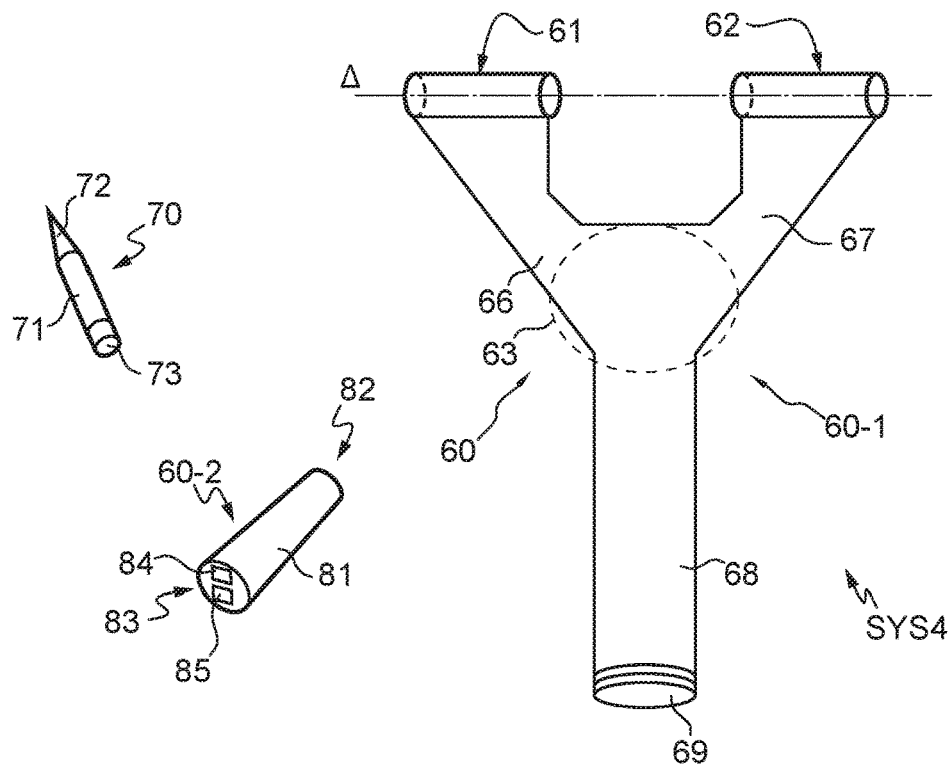
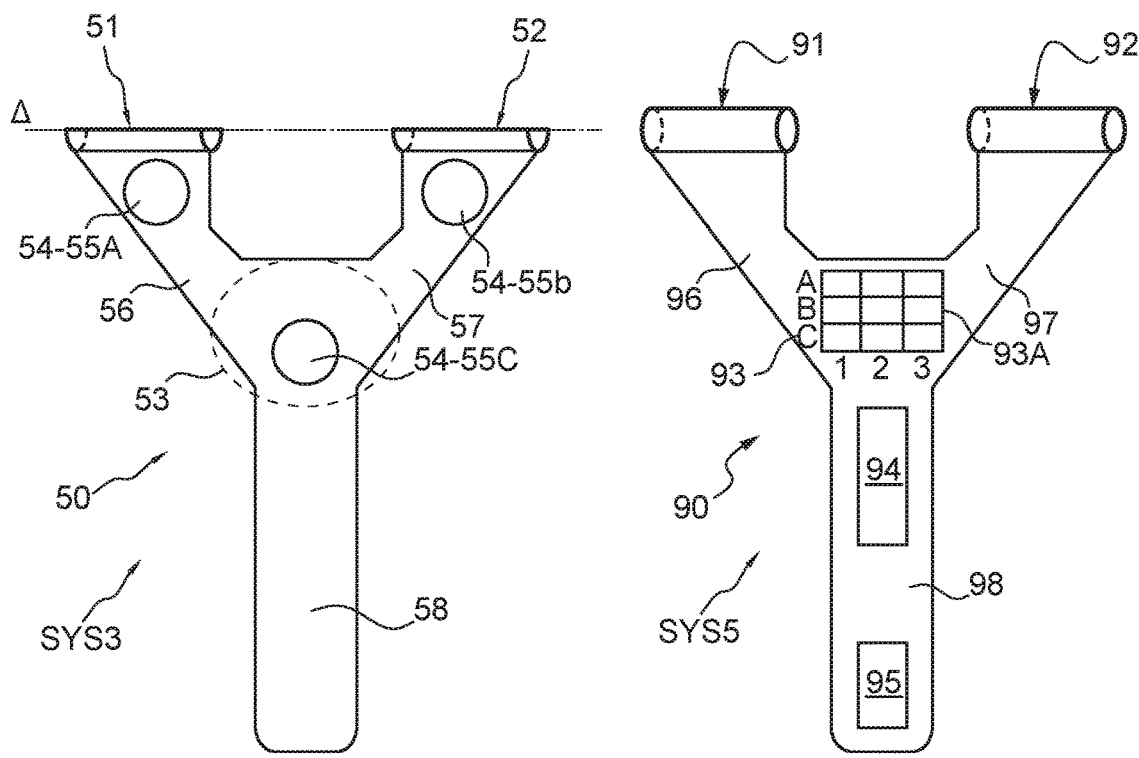
Fig. 6
Fig. 5
Fig. 7

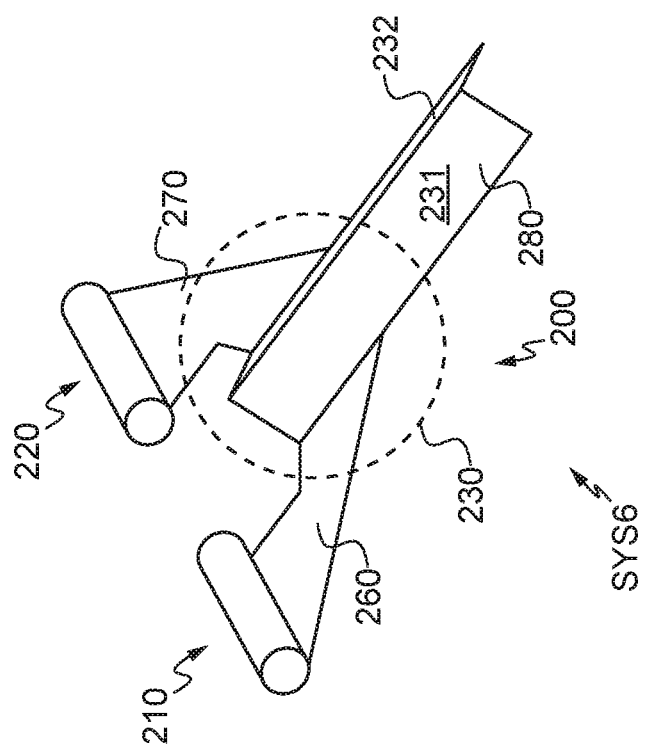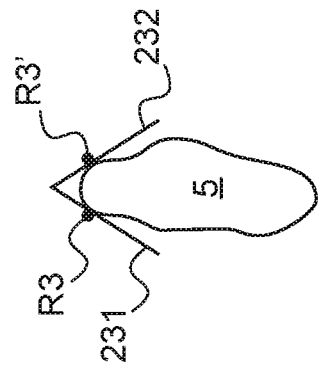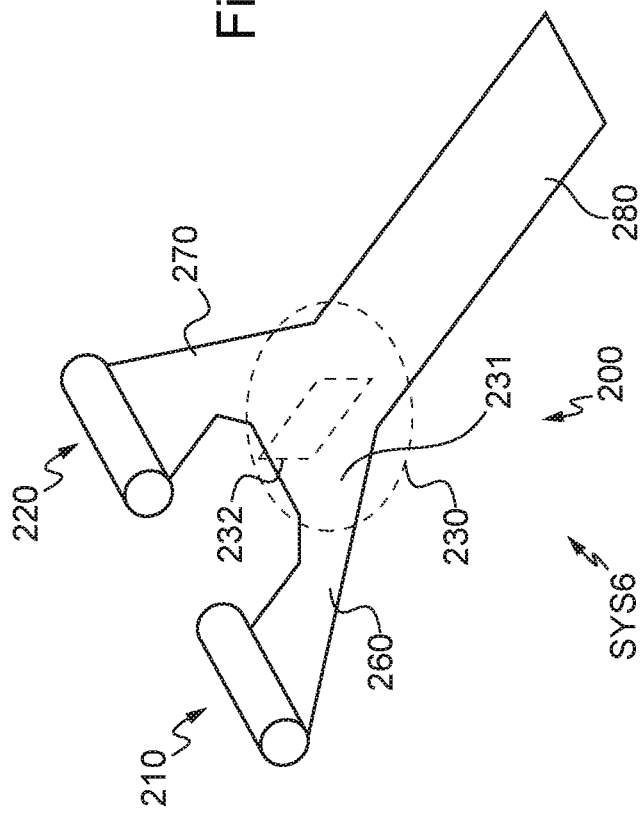
Fig. 8A
Fig. 8B

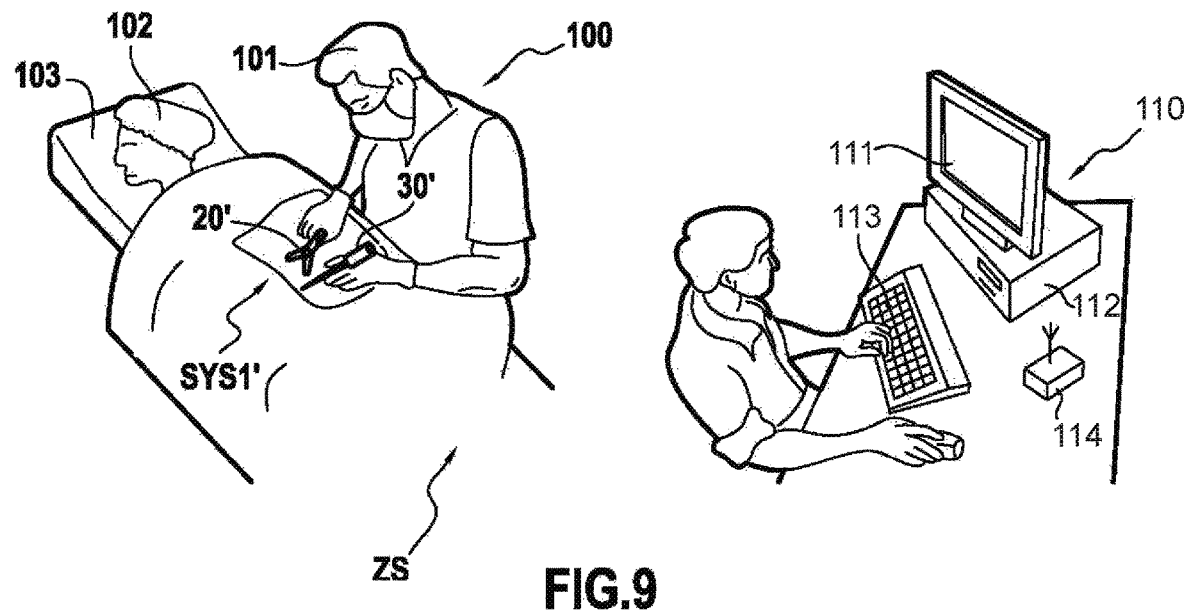
FIG.9
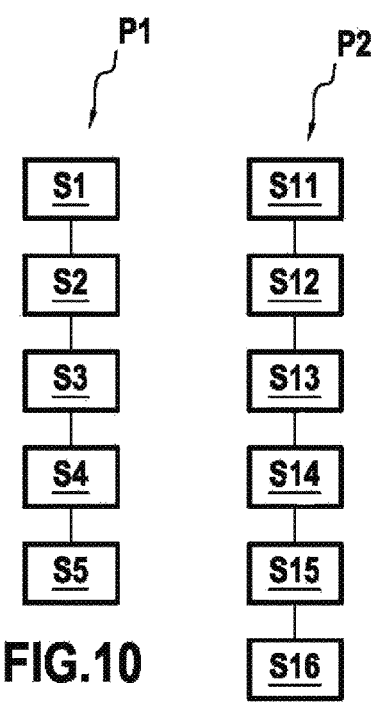
FIG.10
FIG.12
FIG.11

SURGICAL ORIENTATION SYSTEM USING BONE GEOMETRY FOR REPEATABLE POSITIONING

TECHNICAL FIELD

The present invention relates to a surgical orientation system and an ancillary instrument that can be used within the scope of such a system.

CONTEXT OF THE INVENTION

The internal skeletal structure of a mammal, human or animal, is sometimes composed of about a hundred bones or more. The spinal column is a chain of bones or vertebrae allowing a certain flexibility and freedom of movement, while protecting the nerve and vascular structures inside and around the spinal column. The spinal column starts at the base of the skull, extends to the pelvis and is composed of four regions—cervical, thoracic, lumbar and pelvic.

FIGS. 1A, 1B respectively show a view from above and a view from the side of vertebrae 1 that are typically human (thoracic on the left and lumbar on the right). The vertebra 1 comprises: a vertebral body 2 orientated towards the front; a vertebral foramen 3 in the form of a hole allowing the spinal cord to pass through; two transverse processes 4A, 4B, orientated towards the back and outwards; a spinous process 5 between the transverse processes 4A, 4B and orientated downwards; two laminae 6A, 6B which connect the transverse processes 4A, 4B to the spinous process 5; two pedicles 7A, 7B which connect the vertebral body 2 to the transverse processes 4A, 4B; two upper articular facets 8A (not shown), 8B and two lower articular facets 9A (not shown), 9B which allow articulation of the vertebrae 1 to each other.

The normal or ideal vertebral alignment can be disturbed due to a trauma or a disease, for example scoliosis. The vertebrae can pivot about three axes (X, Y, Z), sometimes requiring a surgical operation in order to correct the anomalies and re-establish an ideal, or at the very least a better, alignment of the spinal column.

In this case at least two adjacent vertebrae 1 are generally fused to each other by a method in which a surgeon operates on the patient, generally from the back, determines an entry point 10 and bores holes 11 in the pedicles 7A, 7B of the vertebrae 1. The holes are bored with an axial angle alpha α (the angle relative to the plane XZ) and a sagittal angle beta β (the angle relative to the plane XY), shown in FIGS. 1A, 1B respectively.

Next pedicle screws 12 comprising U-shaped ends 13 are inserted into the holes 11 (for reasons of clarity in FIG. 1A, a single entry point 10, hole 11, pedicle screw 12, and end 13 are shown). The ends 13 receive connecting elements (not shown), for example bars, which make it possible to reduce deformation and fuse the vertebrae 1 together.

Next, the connecting elements are connected between the pedicle screws of two adjacent vertebrae 1 in order to correct, gradually, the alignment of the spinal column, which is based on approximate correction objectives for each level of the spinal column and are derived from medical images (electromagnetic 'X' rays, tomodensitometriy, magnetic resonance imaging, etc.) taken preoperatively, i.e. before a surgical operation. As a result, all the bored holes 11 and the pedicle screws 12 placed in the vertebrae 1 must be carefully positioned and aligned in order not to injure the adjacent nerve and vascular structures. If the pedicle screw 12 is wrongly positioned and leads to a risk of lesion to the nerves, the spinal cord and the blood vessels, a second operation is required, leading to additional costs and risks.

Guidance systems have been developed to aid the surgeon to bore the holes 11 in the vertebra 1 and accurately place the pedicle screws 12. For example, the publication WO 2016/102898 describes tools, accessories, or ancillary surgical instruments, to indicate in advance the right path for the surgeon relative to the images taken prior to operation so as to take into account the position of the patient during the operation.

According to this publication, an ancillary surgical instrument comprises a first contact point configured to come into contact with a first reference point of an operating area; a second contact point configured to come into contact with a second reference point of the operating area; and a contact area configured to come into contact with a third reference point of the operating area;

The ancillary instrument further comprises a means for determining an orientation reference frame of the ancillary instrument in a Galilean orientation reference frame; and a means for communicating the orientation reference frame determined by its proper positioning on the vertebra.

For example, a Y-shaped ancillary instrument is provided in which the first and second contact points are formed using straight ridges provided at the ends of two branches of the Y. The two contact points are applied on the two corresponding first reference points before pivoting the ancillary instrument around the axis formed by the two contact points to come to apply the contact area on the third reference point.

More generally, such an ancillary instrument enables any operator performing an operation, not necessarily a surgical operation, to be guided in an operating area, for example on a mechanical part of which it is desired to know the precise orientation in a Galilean reference frame.

Although the ridges forming contact points may be provided with non-slip "spikes", the pivoting of the ancillary instrument while maintaining the two contact points applied on the corresponding reference points proves to be risky and requires high dexterity by the operator or surgeon. Furthermore, the positioning of the ancillary instrument is difficult to achieve on the two contact points exactly as determined initially.

There results from this a lack of repeatability for the operator of the exact positioning of the ancillary instrument on the reference points. This lack may give rise to an erroneous estimation of the reference frame for the vertebra, detrimental to the accurate performance of the surgical act or mechanical work.

As a result, there is a need for simple systems and tools for assisting the operator or surgeon which enable positioning that is more accurate and less dependent on the operator of the ancillary instrument, to determine, with better repeatability, the orientation of the vertebra during the surgery.

SUMMARY OF THE INVENTION

The present invention is directed to solving the above limitations of the known tools.

In this context, embodiments of the invention relate to an ancillary surgical instrument comprising at least:
  a first contact part configured to come into contact with a first reference area of an operating area;
  a second contact part configured to come into contact with a second reference area of the operating area;
  a third contact part configured to come into contact with a third reference area of the operating area; and a means for determining an orientation reference frame of the ancillary instrument in a Galilean orientation reference frame.

In this ancillary surgical instrument, at least one of the first and second contact parts comprises a concave or convex end, for example curved or bent, configured to come into contact with at least two reference points in the first or second corresponding reference area which is of convex or concave shape respectively (that is to say of substantially complementary shape to the end considered).

By way of example, the ancillary instrument may be the shape of a Y provided with a handle and two cylinders at the ends of two of the branches, such that each cylinder comes to be accommodated in a concave area of the vertebra, for example the laminae. The positioning of the cylinders in the concave areas is naturally made taking into account their respective geometries. The contact points are then those actually intended initially.

Another example is an ancillary instrument in the shape of a Y provided with a handle and two channel-shaped members at the ends of two of the branches, such that each channel-shaped member comes to envelope a convex area of the vertebra, for example the transverse processes.

It can be understood that the contact points are formed at the location of the concave/convex surface of the cylinder or of the channel-shaped member (and not on a ridge delimiting an end of these).

As shown by these two examples, the present invention takes advantage of the concavity/convexity of the bone geometries to create, using the convex/concave end, a repeatable positioning of the ancillary instrument and a guide for rotation thereof towards the position providing the contact with the third contact part. As a matter of fact, the contact points generated by the two ends make it possible for example to define at the very least a pivotal link between the ancillary instrument and the operating area.

The rotation between the convex part and the corresponding concave part (based on the two contact points indicated) makes the rotation of the ancillary instrument secure. The operator can thus concentrate on the placing in contact of the ancillary instrument at the location of the third contact area.

Greater accuracy of positioning, better reproducibility of the operations and a reduction in the manipulation time of the ancillary instrument are thus obtained.

Optional features of the ancillary surgical instrument are furthermore defined in the dependent claims.

According to one embodiment, the first and second contact parts each comprise a concave or convex end configured to come into contact with at least two reference points of the corresponding convex or concave reference area. This provision provides still better security in the positioning of the ancillary instrument, while freeing the operator from checking the continuous contact between the two first contact parts and the operating area. As a matter of fact, dual guiding by rotation is thus obtained.

According to one embodiment, the two ends are of curved cross-section with substantially coaxial generatrices. The two ends may both be concave, both convex or of a different type.

This provision facilitates the rotation, and thus the rocking/pivoting, of the ancillary instrument to seek contact by the third contact part avec with the operating area. As a matter of fact, rotation of the ancillary instrument around this common axis, by the two guide areas, is thus obtained.

According to another embodiment, the two ends have curved (concave or convex) cross-sections and have longitudinal cross-sections which belong to the same conic section. The most classic examples of conic sections are the circle, the ellipse or the parabola.

This provision facilitates the rotation of the ancillary instrument in a plane containing the ancillary instrument (in its substantially planar form as illustrated below). This ease of rotation may for example compensate for a defect in rocking/pivoting on account of undesirable contacts with the operating area.

According to one embodiment, the other contact part of the first and second contact parts is formed by a straight ridge or a pointed member configured to come into contact with a single reference point of the corresponding reference area. This configuration makes it possible to adapt to anatomical asymmetry (either resulting from malformation, or on account of the asymmetric operating area considered).

According to one embodiment, the convex end comprises a member in the form of a roll, roller, cylinder or sphere (that is to say a convex form that is substantially regular, allowance being made for manufacturing uncertainties) configured to engage in the corresponding concave reference area, or the concave end comprises a channel-shaped member (typically an end wall that is semi-cylindrical or substantially semi-cylindrical, that is to say a longitudinally truncated hollow cylinder) or spherical dome (also a substantially regular shape), configured to engage on the corresponding convex reference area.

These regular forms in particular enable regular rotation, without modifying the at least two contact points (three contact points for a sphere for example) for each end. The manipulation comfort for the operator is thus improved. Preferably, the two ends are formed from coaxial members, ensuring this regular rotation around the same axis.

According to one embodiment, the first and second contact parts comprise convex or concave members of the same shape (but potentially of different dimensions to cater to anatomical variations) at their end to come into contact with their respective reference area. This contributes to a rotation or to a regular rocking of the ancillary instrument, for the operator.

Of course, as a variant, members of different shapes may be used to adapt to asymmetric anatomies, as already evoked above.

According to one embodiment, the member forming a convex or concave end is rotatably mounted on the ancillary instrument. It may for example be a roller or rotary cylinder, or a rotary channel-type cross-section.

This provision makes it possible to keep the two contact points unchanged for each concave/convex end in particular in case of rotation around the axis of revolution (or generatrix) of that end. This therefore avoids any risk of sliding or slipping of the contact points already established on rocking. The manipulation comfort for the operator is thus further improved.

According to one embodiment, the convex or concave end has a radius of curvature greater than a local radius of curvature (that is to say in the contact area) of the corresponding concave or convex reference area.

This provision contributes to there being only two contact points between the end and the facing operating area, taking into account the anatomical irregularities of the latter. The rotational guiding and thus the ease of manipulation are improved.

According to one embodiment, the third contact part is configured to come into contact with the third reference area by rocking of the ancillary instrument while the first and second contact parts are in contact with the first and second reference areas respectively. In particular the concave or convex contact part forms a contact at two points with the corresponding reference area.

According to one embodiment, the concave or convex end comprises a surface which has a curved cross-section around an axis of revolution, and the rocking takes place around the axis of revolution, for example the rotational axis of a member forming the convex or concave end rotatably mounted on the ancillary instrument. Preferably, the ends forming the first and second contact parts are of the same type, with collinear axes of revolution, to enable easy rotation.

According to one embodiment, the first contact part, the second contact part, the third contact part, the means for determining and possibly a means for communicating discussed below are incorporated into a single part of the ancillary instrument.

According to one embodiment, the first contact part, the second contact part and the third contact part are incorporated into a first part of the ancillary instrument, and the means for determining and possibly the means for communicating are incorporated into a second part able to be implanted on the first part, that is to say be fixedly secured to the first part of the ancillary instrument using mechanical means.

According to one embodiment, the third contact part is a substantially planar tangential contact area.

According to one embodiment, the third contact part is formed by a concave or convex area configured to come into contact with at least two reference points of the third reference area which is respectively of convex or concave shape. This arrangement greatly facilitates the exact positioning of the ancillary instrument on the operating area, taking into account the reference points (determined for example in a preoperative phase by the computer). Obtaining the orientation reference frame with exact positioning is thus highly reproducible, these two contact points in the third contact part making it possible to dispel the uncertainty in the positioning of the ancillary instrument defined by the rotational axis created by the contact points of the first and second contact parts.

According to one embodiment, the third contact part is formed by two planar surfaces, each configured to come into contact with a single reference point in the third reference area. This configuration is simple to implement at the location of the third contact part. Furthermore, a planar surface facilitates the sliding of the ancillary instrument along the corresponding single reference (contact) point, to position the other surface in contact with the other single reference point. Thus, the positioning of the ancillary instrument is totally controlled and reproducible.

According to one embodiment, the third contact part has a V-shape or inverted V-shape, depending on whether the third reference area is concave or convex. Of course, variant shapes may be provided if they enable a contact at two reference points between the third contact and reference parts: a groove of any shape, for example parabolic or inverted parabolic.

According to one embodiment, the first and second contact parts and one of the two planar surfaces of the third contact part form part of a same single-unit part, and the other planar surface of the third contact part is formed by a mechanical part mounted on the single-unit part (and preferably fixedly secured thereto). This makes it easy to design this third contact part (enabling accurate positioning) based on a planar surface, such as provided in the known ancillary instruments.

According to one embodiment, the orientation reference frame of the ancillary instrument allows an orientation reference frame of the operating area to be determined with respect to the Galilean orientation reference frame for example by means of a rotation matrix. According to an embodiment, the ancillary instrument is Y-shaped (the shape of the letter wye) and comprises:
- at least two branches at the ends of which the first and second contact parts are disposed;
- a third branch in the form of a handle; and
- a central area having a lower face which forms the third contact part.

According to one embodiment, the ancillary instrument moreover comprises validating means of the third contact part.

According to one embodiment, the third contact part is transparent and arranged in a form that comprises a grid and which is marked in order to enable an operator to determine exactly where the third contact part is in contact with a point of the third reference part. This makes it possible to fully determine the position and the orientation of the ancillary instrument.

According to one embodiment, the length, the angle, and/or the inclination of at least one branch of the ancillary instrument can be adjusted.

According to one embodiment, the means for determining the orientation reference frame is a device comprising at least one of the following components: a tri-axial accelerometer, a tri-axial magnetometer, and/or a tri-axial gyroscope.

According to one embodiment, the means for determining the orientation reference frame is a device comprising at least three non-aligned optical markers, configured to be visible by at least one camera filming the operating area.

According to one embodiment, the ancillary instrument further comprises a means for communicating the determined orientation reference frame.

According to one embodiment, the means for communicating the orientation reference frame is a visual display.

According to one embodiment, the means for communicating the orientation reference frame is a wired or wireless connection.

Embodiments of the invention moreover relate to an assembly comprising at least two different ancillary instruments according to the invention, the ancillary instruments being designed for operating areas that are different from one another.

Embodiments of the invention moreover relate to a surgical orientation system comprising at least one ancillary instrument according to the invention and a surgical tool comprising:
- means for determining an orientation reference frame of the tool; and
- means for communicating the orientation reference frame of the tool.

According to one embodiment, the ancillary instrument and the surgical tool are configured to be coupled to one and the same device for determining and communicating an orientation reference frame.

Embodiments of the invention moreover relate to an operating theatre equipped with an ancillary surgical instrument according to the invention and a device for displaying images and data processing comprising:
- a screen or projection means for displaying images taken of the operating area;
- a processor;
- means for entering and manipulating data; and means for receiving data communicated by the ancillary instrument.

Embodiments of the invention moreover relate to a method for the preoperative preparation of a surgical operation, comprising the steps of:

taking at least one three-dimensional image of an operating area;

determining at least two reference points in a first reference area of the operating area, and at least two other reference points of a second reference area (potentially two other pairs of points for the second and third reference areas) of the operating area, from the three-dimensional image. In practice, it may be envisioned for an operator to indicate only the anatomical areas corresponding to the reference areas, and for a computer algorithm to determine the reference points in these areas taking into account the geometrical dimensions of the ancillary instrument to use;

calculating an orientation reference frame by means of the reference points, the orientation reference frame being identifiable subsequently by an ancillary instrument according to the invention; and determining at least one local axis in the reference frame, for a surgical movement to be performed.

Other embodiments of the invention directed to providing simple systems and tools for assisting the (non-surgeon) operator or the surgeon, relate to an ancillary instrument or tool in the form of a compass with two branches. The ancillary instrument comprises at least:

a first branch having a first contact terminal end configured to come into contact with a first reference area of an operating area;

a second branch having a second contact terminal end configured to come into contact with a second reference area of the operating area;

a fixed part relative to which the two branches move to open or close the ancillary instrument, such that, on opening or closing the ancillary instrument, the first and second terminal ends form an axis which is constantly parallel to a reference axis of the fixed part; and a means for determining an orientation of the ancillary instrument. This is preferably the orientation of the axis formed by the first and second ends.

As referred to below, the means for determining an orientation of the ancillary instrument, typically an inertial measurement unit, makes it possible to determine two orientations on making two measurements, and thereby determine an orientation reference frame of the ancillary instrument (i.e. an operation reference frame) in a Galilean reference frame.

This tool is simple to manipulate for an operator or a surgeon. Furthermore, the geometrical property of the terminal ends (forming a constantly parallel axis) makes it possible to utilize a single means for determining an orientation for determining an operation reference frame of the operating area, within a Galilean orientation reference frame. Any need for calibration relative to two sensors that would be mounted on each of the branches is thus dispensed with.

To that end, these embodiments also provide a method of determining an operation reference frame of an operating area in situ, in a Galilean orientation reference frame, using an ancillary instrument of two-branched compass type equipped with a means for determining an orientation of the ancillary instrument, the two branches of the ancillary instrument moving, on opening or closing the ancillary instrument, such that their terminal ends form an axis which is constantly parallel to a reference axis of a fixed part of the ancillary instrument. The method comprises the steps of:

obtaining, from the means for determining an orientation, at least two orientations that are not parallel in the Galilean orientation reference frame between two pairs of reference areas within the operating area, by successively positioning the two terminal ends of the ancillary instrument on each of the two pairs of reference areas; and determining the operation reference frame from the two orientations obtained.

Thus, the operator can determine an operation reference frame, within the Galilean reference frame, by operations that are simple and few in number. The measurement of only two orientations via two successive acts of positioning of the compass alone is sufficient.

The method advantageously applies to the determination of reference frames for mechanical parts on which operations requiring accuracy are planned, for example to perform boring operations therein or to place fastening means therein.

By way of example, an operation reference frame may be formed by the plane defined by the two orientations obtained. Furthermore, an operation reference frame axis may be along one of the orientations obtained, for example the first.

Thus, a guiding method is also provided for an operation on an operating area, comprising the steps of:

obtaining at least three reference areas in the operating area;

obtaining an operation reference frame by means of the reference areas;

determining at least one operation axis in the operation reference frame, for an operating movement to perform;

determining in situ said operation reference frame of the operating area in a Galilean orientation reference frame, using the above method; and performing an operating movement on the operating area using an operating tool, at least one axis of the operating tool being determined in the Galilean orientation reference frame and being placed in correspondence with the operation axis in the operation reference frame.

This correspondence may for example be made by conversion of at least one of said axes of a reference frame into the other. Of course, several operation axes (2 or 3) may be determined initially in order to make them correspond exactly to the corresponding axes of the operating tool. Such control of the orientation of the tool may prove important when it is desired to master the positioning and the orientation of a part to fix in the operating area. By way of illustration only, this may be the case of the sensitive positioning of an implant in an anatomical area.

The conversion may simply comprise the application of a rotation matrix to a vector defining either the operation axis, or the axis of the operating tool.

Different versions of the ancillary instrument of compass type may be used.

For example, the first and second branches may be rotatably mounted on the fixed part and be arranged to open or close symmetrically relative to the fixed part. Such a version of the ancillary instrument is easy to use by an operator. Preferably, the means for determining an orientation is of inertial measurement unit type and fixedly mounted to the fixed part. The inertial measurement unit, which is fixed relative to the reference axis, thus makes it possible to know, without calculation or additional means, the orientation between two reference areas in contact with two terminal ends of the compass.

According to a variant embodiment, the first and second branches are branches are mounted to be movable in translation relative to the fixed part and are arranged to slide in translation, possibly symmetrically, relative to the fixed part. In this case, the means for determining an orientation may be of inertial measurement unit type fixedly mounted to the first or second branch, or be fixedly mounted to the fixed part.

In one embodiment, at least one of the two terminal ends, or even both, is formed by a contact point configured to come into contact with a reference point of the corresponding reference area. Thus, as regards the method of determining an operation reference frame in situ, two pairs of reference areas comprise at least three non-aligned reference points, and the terminal ends of the branches of the ancillary instrument are formed by points configured to come into contact with the reference points.

As a variant, at least one of the two terminal ends, or even both, is formed by a concave or convex end configured to come into contact with at least two reference points of the first or second corresponding reference area which is of convex or concave shape respectively. It is to be noted that in this case, the axis which remains constantly parallel may be defined by the centers of the concave/convex ends (for example a central point on the axis of a cylinder or a roller, or the center of a sphere). The different configurations referred to in the above embodiments are applicable to the ends of the ancillary instrument of compass type defined here.

According to one embodiment, the means for determining an orientation comprises at least one of the following components: a tri-axial accelerometer, a tri-axial gyroscope, and/or a tri-axial magnetometer.

In one embodiment, the obtaining of the three reference areas, of the operation reference frame and the determination of the operation axis are carried out on a three-dimensional digital model of the operating area. This provision makes it possible to take advantage of the computation capacities of computer systems.

In one embodiment which is directed to simplifying the operator's operation, performing the operating movement comprises the following steps:
  displaying, on a screen, a three-dimensional digital model of the operating area, said displaying preferably (but not necessarily) being carried out along the operation axis;
  displaying, on the screen, an indicator of an operating point on the operating area and an orientation indicator, in the display reference frame, of the operating tool positioned on the operating point; and
  performing the operating movement on the operating area when the two indicators coincide.

It is to be noted that additional indicators (for example rotation indicators) can make it possible to place in correspondence a second axis of the operating tool (first additional indicator) with a second operating axis (second additional indicator).

Embodiments of the invention moreover relate to a non-transitory medium which can be read by a computer and which comprises a program of computer-executable instructions for carrying out one of the methods according to the invention.

BRIEF DESCRIPTION OF THE DRAWINGS

Other particular features and advantages of the present invention will become apparent from the detailed description given with reference to the Figures in which:

FIGS. 1A, 1B, previously described, respectively show a top view and a side view of typical lumbar and thoracic vertebrae, FIG. 2B shows two vertebrae, thoracic and lumbar, with reference areas for the operation, FIGS. 3A, 3B show respectively a top view and a side view of the ancillary surgical instruments shown in FIG. 2A in use on thoracic and lumbar vertebrae, FIG. 5 is a diagrammatic representation of a surgical orientation system according to another embodiment, FIG. 6 is a diagrammatic representation of a surgical orientation system according to another embodiment, FIG. 7 is a diagrammatic representation of a surgical orientation system according to another embodiment, FIGS. 8A, 8B respectively show a perspective view of an orientation system according to two other embodiments and a cross-section view, at the spinous process, of their use on thoracic and lumbar vertebrae, FIG. 9 shows an operating theatre equipped with a surgical orientation system according to an embodiment, FIG. 10 shows a flow chart of a preoperative phase, FIG. 11 shows a flow chart of a preoperative phase, FIG. 12 shows a non-transitory medium which can be read by a computer and which comprises a program of computer-executable instructions.

DETAILED DESCRIPTION OF EMBODIMENTS

Figure 2A:
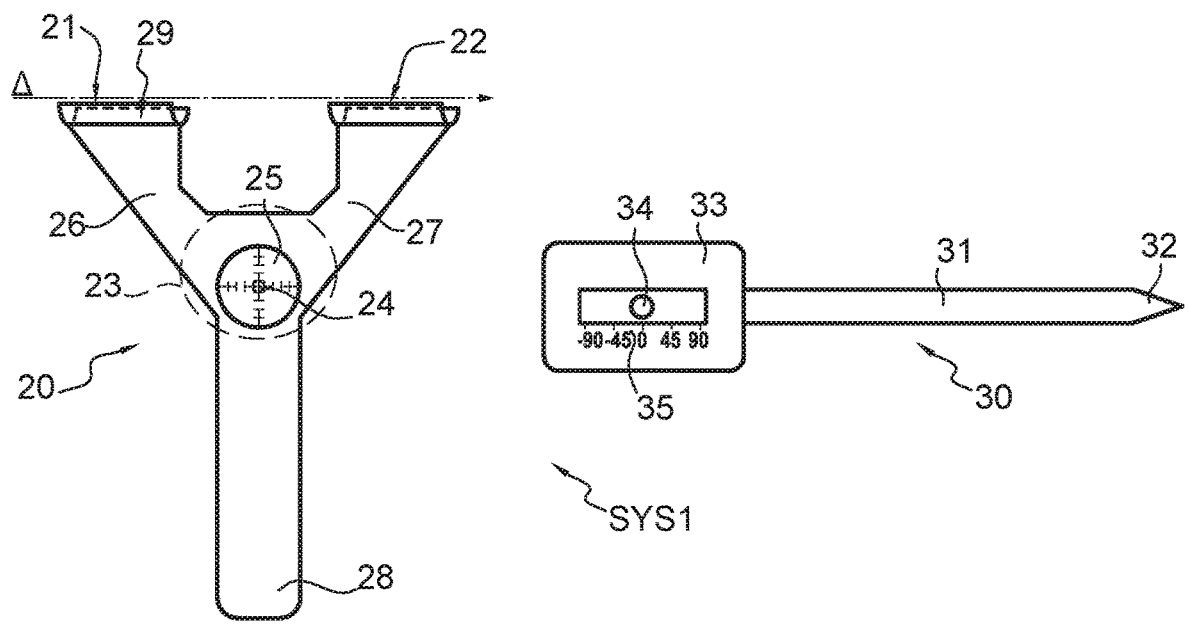
FIG. 2A shows a top view of two surgical orientation systems each comprising an ancillary surgical instrument and a surgical tool according to one embodiment.

FIG. 2A shows two surgical orientation systems SYS1, SYS2 according to embodiments.

The system SYS1 comprises a tool 20 (hereafter "ancillary instrument") and a surgical tool 30, for example for drilling.

The ancillary instrument 20 comprises: at least two contact parts 21, 22; a third contact part, here a planar tangential contact area 23; a means 24 for determining an orientation reference frame RA of the ancillary instrument and a means 25 for communicating the orientation reference frame RA of the ancillary instrument. The orientation reference frame RA of the ancillary instrument 20 can be considered as an orientation reference frame RO of an operating area ZO (for example the vertebra 1) and as a result makes it possible to know the orientation reference frame RO in a Galilean orientation reference frame RS, for example of an operating theatre ZS (shown in FIG. 9). Hereinafter, the term orientation reference frame RO of the operating area will be used.

In this embodiment, the ancillary instrument 20 is Y-shaped (the shape of the letter wye), the contact parts 21, 22 being concave members, in particular coaxial members that are channel-shaped (i.e. semi-cylindrical walls) positioned at the ends of a first branch 26 and of a second branch 27 respectively, and a third branch 28 serving as a handle. The branches 26, 27 are the upper left and right ends of the Y respectively, the branch 28 is the lower central end of the Y, and the third contact part 23 is arranged at the center of the Y and comprises a lower face that is more or less planar. The inside wall 29 of the concave members 21, 22 is preferably smooth in order to enable reference points of the operating area to slide on manipulating the ancillary instrument 20 as explained below.

As shown on the left part of the FIG. 2B, the operating area ZO (here a thoracic vertebra 1) comprises at least three reference areas Z1, Z2, Z3 to use with the system SYS1. In the case of a thoracic vertebra 1, the areas Z1, Z2 are constituted for example by posterior walls of the transverse processes 4A, 4B respectively (downwardly oriented convex walls of FIG. 1A), and are very easy to find with the naked eye, in particular by an experienced surgeon. The contact area Z3, here simplified to a single point R3, is disposed on the spinous process 5 in a tangential area, as will be explained later. As a result, the concave contact parts 21, 22 are each configured to come into contact with the convex reference areas Z1, Z2 respectively and the third contact part 23 is placed on the point R3 in order to determine a system of coordinates or "orientation reference frame" RO of the operating area ZO with respect to the orientation reference frame RS of the operating theatre ZS.

The system SYS2 also comprises a tool 20 (hereafter "ancillary instrument") and a surgical tool 30, for example for drilling.

Compared to SYS1, the system SYS2 comprises a Y-shaped ancillary instrument 20 of which the contact parts 21, 22 are convex members, in particular coaxial members of roll, cylinder or roller form (that is to say substantially cylindrical walls that are not necessarily closed) positioned at the ends of the branches 26, 27 respectively.

The convex members 21, 22 may be smooth in order to enable sliding of reference points of the operating area on manipulating the ancillary instrument 20 as explained below. As a variant, these convex members 21, 22 may be rotatably mounted on the ancillary instrument, preferably on the same axis Δ, in which case their surfaces may be provided with a non-slip coating in order to ensure sustainable contact with points of the corresponding reference areas Z1, Z2.

On the right part of FIG. 2B, an operating area ZO (here a lumbar vertebra 1) again comprises at least three reference areas Z1, Z2, Z3 to use with the system SYS2. In the case of this lumbar vertebra 1, the areas Z1, Z2 are constituted for example by laminae 6A, 6B respectively (forming concave cavities under the transverse processes), and are very easy to find with the naked eye, in particular by an experienced surgeon. The contact area Z3 is again a single point R3 disposed on the spinous process 5 in a tangential area. As a result, the convex contact parts 21, 22 are each configured to come into contact with the concave reference areas Z1, Z2 respectively and the third contact part 23 is placed on the point R3 in order to determine a system of coordinates or "orientation reference frame" RO of the operating area ZO with respect to the orientation reference frame RS of the operating theatre ZS.

The surgical tool 30 is for example a tool for boring the vertebra 1, and comprises: a shank 31; a point 32 at the front end of the shank; a handle 33; a means 34 for determining an orientation reference frame RT of the tool; and a means for communicating the orientation reference frame RT of the tool.

In the simplest case, the determining means 24, 34 are spirit levels, also known as inclinometers, and the communicating means 25, 36 are visual indicators, for example figures marked around the spirit level or even a simple circle at the center of the level.

As a variant, the determining means 24, 34 may be "MEMS" or "microelectromechanical systems" which determine the plane of the ancillary instrument 20. These means can comprise a tri-axial accelerometer, a tri-axial gyroscope, and/or a tri-axial magnetometer, as known to a person skilled in the art and thus not explained in more detail. The communication means 45 may be a wired (cable) or wireless (contactless) connection, for example by Wi-Fi or Bluetooth.

In the embodiments illustrated in FIG. 2A, the two concave/convex members 21, 22 are of substantially regular shape around an axis, and their generatrices are coaxial (along the axis Δ).

Figure 3B:
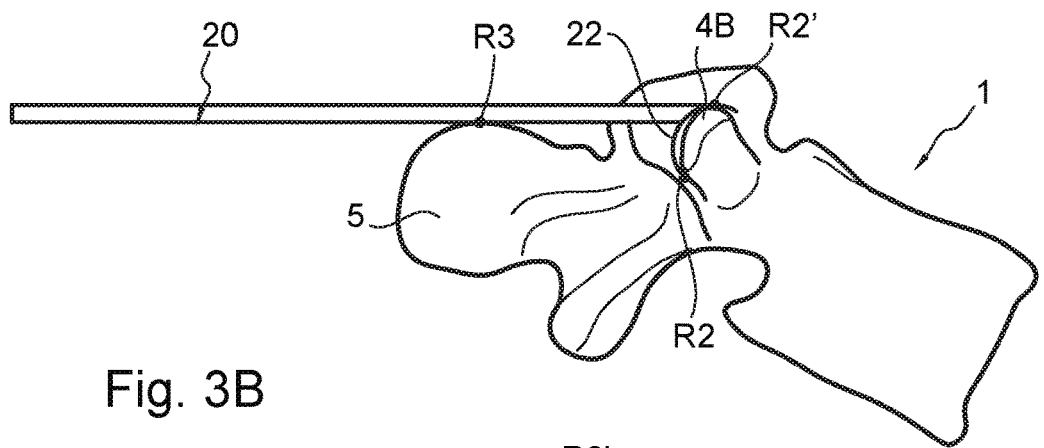

The left parts of FIGS. 3A, 3B respectively show a top view and a side view of the ancillary instrument 20 of SYS1 laid on a thoracic vertebra 1. The right parts of FIGS. 3A, 3B respectively show a top view and a side view of the ancillary instrument 20 of SYS2 laid on a lumbar vertebra 1.

The dimensions of the ancillary instrument 20 are configured for the envisioned application, for example approximately 10 cm wide, 15 cm long and 0.50 cm thick for operations on the human spinal column, with a diameter for the channels of approximately 1 cm.

In a preoperative phase, images are obtained, for example of the entire spinal column, in order to make three-dimensional reconstructions of the operating area. Then, for each vertebra, the reference areas Z1, Z2, Z3, are determined, in order to define the orientation reference frame RO of the operating area. For an operator, this may be a matter of indicating areas of interest. Next, for example two reference points R1, R1', R2, R2' are determined for each of the areas Z1, Z2. These points are easy to determine by a computer given the 3D representation of the vertebra considered and of the ancillary instrument used. They may for example be the most protruding or protuberant points (outwardly or inwardly) which will come into contact with the members 21, 22 of the ancillary instrument. In other words, they are contact points taking into account the dimensions of the selected ancillary instrument (diameter of the convex/concave part, etc.).

In some embodiments, point R3 is a point in the tangential area Z3, which will be more difficult to determine with the naked eye but easy to determine by a computer program, which will enter into contact with the third contact part 23 merely by laying the ancillary instrument 20 on the area Z3.

FIG. 3B show that the concave contact part 22 enters into contact solely with two points R2, R2' of the reference area Z2 formed by the transverse processes 4B (although the Figure shows contact points in the same transverse plane, these may be longitudinally offset). The same applies for the concave contact part 21 (not shown). The choice of concave contact parts 21, 22 having a greater radius of curvature than the local radius of curvature of the corresponding convex reference areas Z1, Z2 ensures, thanks to the anatomical irregularities of the reference area, that the contact is made solely at two points. The local radius of curvature may match the radius of an approximation of the reference area, that is to say substantially the area in which one of two contacts will take place. The radius of the concave part and the local radius of curvature are assessed based on the same cross-section.

In similar manner, the convex contact part 22 enters into contact solely with two points R2, R2' of the reference area Z2 formed by the lamina 6B (the same applying for the convex contact part 21 not shown). The choice of convex contact parts 21, 22 having a greater radius of curvature than the radius of curvature of the corresponding concave reference areas Z1, Z2 ensures that the contact is made solely at two points.

It can be seen from these Figures that the rotational rocking of the ancillary instrument 20 is facilitated by guiding thereof by the reference points R1, R1', R2, R2', the latter making it possible to define the rotational axis Δ in relation to the bone.

Next, in the case of placing pedicle screws, the entry of the optimum screwing directions of the pedicle screws 12 makes it possible to define a directing vector for each pedicle screw.

Figure 4:
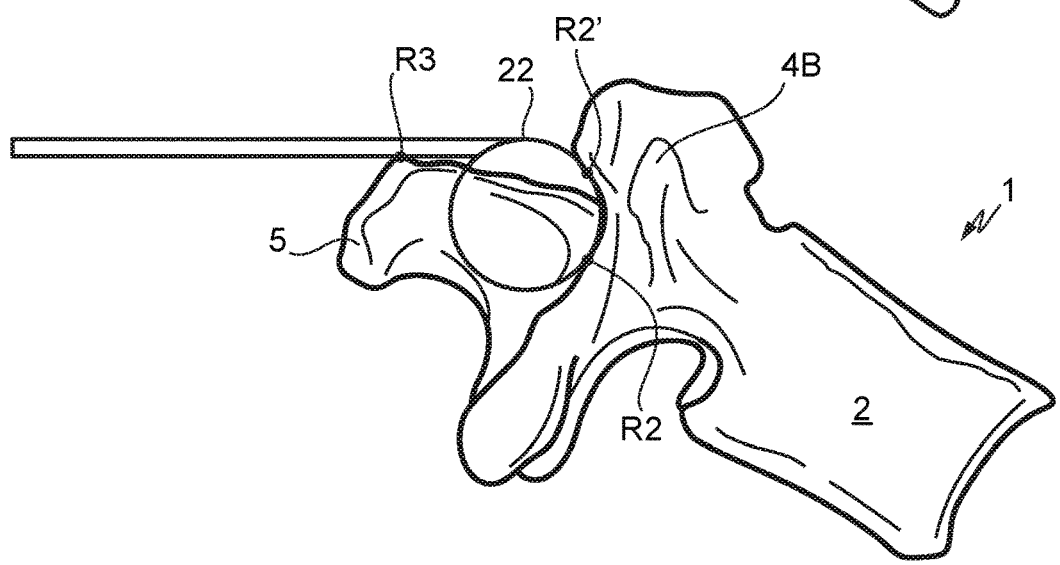
FIG. 4 shows an orientation reference frame of an operating theatre and an orientation reference frame of an operating area.
Figure 4:
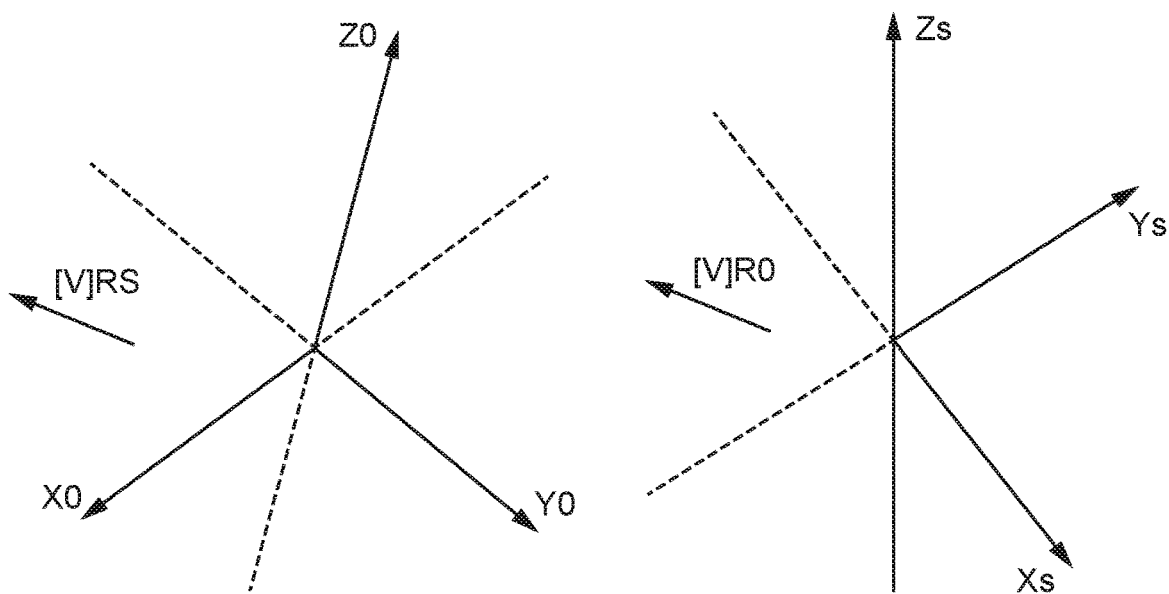

With reference to FIG. 4, which shows the orientation reference frame RO of the operating area and the Galilean orientation reference frame RS of the operating theatre, each orientation reference frame RO, RS comprises three axes, Xo, Yo, Zo; Xs, Ys, Zs respectively. An arrow [V]ro (or "local reference frame") shows a directing vector V for a surgical movement (for example placing a pedicle screw) expressed in the orientation reference frame RO of the operating area (currently in the vertebra). The orientation reference frame RO of the operating area is not necessarily aligned with the orientation reference frame RS of the operating theatre, as shown in FIG. 4.

Next, during the pre-operative phase, the surgeon positions the ancillary instrument 20 on the vertebra 1, as shown in FIGS. 3A, 3B, by placing the contact parts 21, 22 in contact with the reference areas Z1, Z2, that is to say until a contact is obtained with the reference points R1, R1' and R2, R2' respectively, and then by rocking, by rotating, the ancillary instrument 20 while the contact parts 21, 22 are in continuous contact with the reference areas respectively, so as to place the contact part 23 on the reference area Z3. It is noted that the rocking is carried out by rotation around the axis of the contact parts 21, 22, that is to say around the axis of revolution of the curved portions forming those contact parts (the axis Δ).

The orientation reference frame RO of the operating area ZO is then determined with respect to the orientation reference frame RS of the operating theatre, using the determining and communicating means 24, 25 of the orientation reference frame RO of the operating area ZO.

A rotation matrix Mrors, which expresses the orientation reference frame RO in the orientation reference frame RS, is defined. A directing vector [V]rs in the orientation reference frame RS of the operating theatre ZS can be established with respect to the orientation reference frame RO of the operating area ZO, established beforehand, according to the following equation:

$$[V]rs = Mrors \cdot [V]ro \quad \text{[equation 1]}$$

Lastly, the surgical tool 30 determines and communicates, using the determining and communicating means 34, 35 of the orientation reference frame RT of the tool, its orientation in real time, in particular the orientation of its shank 31, in the orientation reference frame RS of the operating theatre. The dynamic orientation of the shank 31 with respect to the ideal orientation of the pedicle screw to be placed, allows the surgeon to adapt the orientation of the tool 30 to make it correspond to the orientation of the directing vector [V]ro expressed in the Galilean orientation reference frame RS (i.e. [V]rs).

As a variant, the directing vector [V]ro and the orientation of the tool 30 may be converted for a different reference frame, for example a reference frame used for a display, to enable the surgeon to see when the orientation of the tool 30 corresponds to the orientation of the surgical movement, in that reference frame.

FIG. 5 shows a top view of a surgical orientation system SYS3 according to another embodiment. The system SYS3 comprises an ancillary instrument 50 and a surgical tool (not shown for reasons of simplicity).

The ancillary instrument 50 comprises: at least two contact parts 51, 52, which are concave and/or convex as described earlier; a third contact part 53, for example tangential; and determining and communicating means 54-55A, 54-55B, 54-55C for the orientation reference frame RA (RO). The means 54-55A, 54-55B, 54-55C are non-aligned optical markers intended to be captured by a plurality of cameras which film the operating theatre ZS in real time, in order to find the positions of the tools with respect to the model.

Similarly to the ancillary instrument 20 described in relation to FIG. 2A, in this embodiment, the ancillary instrument 50 is Y-shaped (the shape of the letter wye), the contact parts 51, 52 being concave and/or convex members (for example one channel-shaped and the other cylindrical) of a first branch 56 and of a second branch 57 respectively, and a third branch 58 serving as a handle. The branches 56, 57 are the upper left and right ends of the Y respectively, the branch 58 is the lower central end of the Y and the contact part 53 is disposed at the center of the Y.

The surgical tool can be similar to the tool 30 described in relation to FIG. 2A (comprising inclinometers), comprising MEMS determining and communicating means which are wired or wireless (contactless) or even comprise optical markers.

Moreover, it is not obligatory that the surgical tool comprises such determining and communicating means. In this case, it can be a simple standard surgical tool.

FIG. 6 shows a perspective view of a surgical orientation system SYS4 according to another embodiment. The system SYS4 comprises an ancillary instrument 60 and a surgical tool 70. In this embodiment, the ancillary instrument 60 is divided into two parts, a first part 60-1 for making contact with the operating area, and a second part 60-2 for determining and communicating the orientation reference frame of the operating theater.

The first part 60-1 of the ancillary instrument 60 is similar to any one of the ancillary instruments 20, 50 described above, and comprises: at least two contact parts 61, 62; a tangential contact part 63; branches 66, 67, 68; and an end 69 to receive the second part 60-2.

The second part 60-2 comprises: a body 81; a hollow front end 82 for receiving the rear end 69 of the first part 60-1; a means 84 for determining the orientation reference frame RA, RT (RO) of the part 60-1 of the ancillary instrument 60; and a means 85 for communicating the orientation reference frame of the ancillary instrument 60.

The surgical tool 70 comprises: a shank 71; a point 72 at the front end of the shank; and a rear end 73.

Preferably, the ancillary instrument 60 and the surgical tool 70 cooperate so that the second part 60-2 of the ancillary instrument 60 can be implanted on the first part 60-1 and the tool 70 in a non-permanent (it can be removed), accurate (no play between the members) and repeatable (reproducible) manner. To this end, the ends 69, 73 of the first part 60-1 of the ancillary instrument 60 and of the surgical tool 70 respectively can comprise protuberances received in a notch inside the hollow front end 82, requiring the second part 60-2 to be implanted in a previously defined manner.

The second part 60-2 is first of all implanted on the end 69 of the first part 60-1 of the ancillary instrument 60. Once the orientation reference frame RA has been determined and communicated, the part 60-1 is set aside and the part 60-2 is removed and placed on the end of the surgical tool 70 to again determine and communicate the orientation RT of the tool 70. This system enables a reduction in cost since a single reference frame determining and communicating device is required, and may be used if the operating area is not likely to change position in the course of operation.

FIG. 7 shows a top view of a surgical orientation system SYS5 according to another embodiment. The system SYS5 comprises an ancillary instrument 90 and a surgical tool (not shown for reasons of simplicity).

The ancillary instrument 90 comprises at least two contact parts 91, 92; a third contact part 93, for example tangential; means 94 for determining the orientation reference frame, for example a "MEMS", system, and means 95 for communicating the orientation reference frame for example a wireless (contactless) link.

Like the ancillary instrument 50 described in relation to FIG. 5, in this embodiment, the ancillary instrument 90 is Y-shaped (the shape of the letter wye) with the concave and/or convex contact parts (cylinders in the FIG. 91, 92 being disposed at the end of a first branch 96 and of a second branch 97 respectively, and a third branch 98 serving as a handle.

The branches 96, 97 are the upper left and right ends of the Y respectively, the branch 98 is the lower central end of the Y and the contact part 93 is disposed at the center of the Y.

Figure 2A:
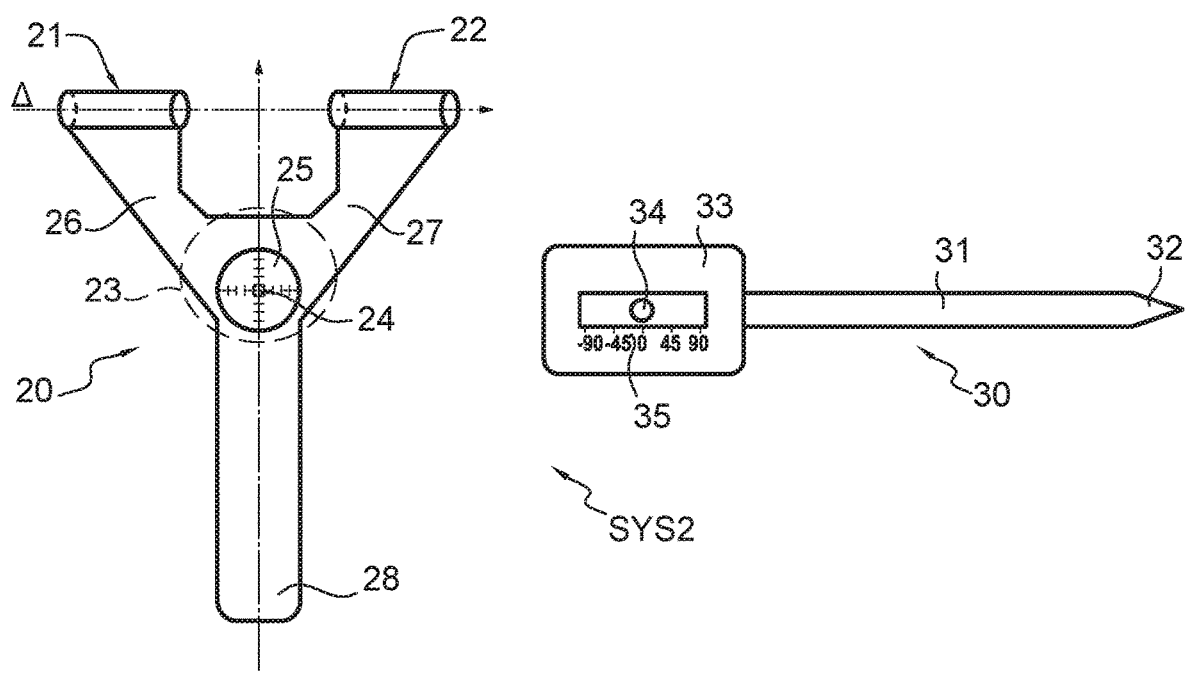

The ancillary instrument 90 moreover comprises validating means 93A of the tangential contact part 93. To that end, in this embodiment, the contact part 93 is transparent and arranged in a form that comprises a grid and which is preferably marked for example with FIGS. 1 to 3) and letters (A to C), in order to enable a surgeon to determine exactly where the tangential area is in contact with the reference point R3 of the third reference part Z3. For example, during the preoperative phase, it can be determined that the reference point R3 must be in contact with the area A3 of the tangential area. The contact parts 91, 92 may also be equipped with markers (not shown) in order to facilitate locating the contact points R1, R1', R2, R2'.

In another embodiment, the validation means are a sensitive contact area which detects the contact with the third reference point, and communicates it for example by the communicating means.

FIG. 8A shows perspective views of a surgical orientation system SYS6 according to another embodiment. The system SYS6 comprises an ancillary instrument 200 and a surgical tool (not shown for reasons of simplicity).

The ancillary instrument 200 is Y-shaped and comprises two concave and/or convex first contact parts (cylinders in the FIG. 210, 220 disposed at the ends of a first branch 260 and of a second branch 270 respectively. The two contact parts 210, 220 may be of any type referred to previously. The optional means for determining an orientation reference frame and for communicating are not shown.

The ancillary instrument 200 is distinguished by the geometry of the third contact part 230, which is no longer just a planar surface forming a tangential contact with the operating area. The third contact part 230 is formed by a concave area (as in the Figure) or convex (not shown) configured to come into contact with two reference points R3, R3' of the third reference area Z3 which has an inverted shape, that is to say convex or concave respectively.

In the example of FIG. 1A, the upper surface of the spinous process 5 has a convex shape. A concave third contact part 230 is thus preferably used.

As shown in FIG. 8A, the third contact part 230 may be formed from two planar surfaces 231, 232, preferably disposed as an inverted V or as a T, and each configured to come into contact with a single reference point R3 or R3' of the third reference area Z3.

In the first example of FIG. 8A, the first planar surface 231 is constituted by the central body of the Y-shaped ancillary instrument, meaning that the first and second contact parts 210, 220 (and thus the branches 260, 270) and that planar surface 231 form part of the same single-unit component. The second surface 232 is then constituted by a mechanical component that is mounted (preferably fixedly, and possibly be removably) on the single-unit component forming a Y.

In the other example, the third branch 280 that forms a handle is not planar but is made from two planar plates 231, 232 forming, in cross-section, an inverted V. Thus, the third area is of channel type having an inverted V-shaped profile in cross-section.

FIG. 8B represents a cross-section view of the ancillary instrument 200 in position in the examples of FIGS. 3A and 3B, at the location of the spinous process 5 where the third reference area Z3 is located. The presence of the two contact points R3, R3' (represented here in the same cross-section for reasons of clarity, whereas in practice they may be offset along the longitudinal axis of the spinous process) ensures exact, and thus reproducible, positioning of the ancillary instrument 200 on the operating area, here a vertebra.

The concave or convex area forming a third contact part 230 is not necessarily the junction of two planar surfaces as in FIGS. 8A and 8B. It may for example be an arrangement (channel, cylinder, etc.) having a wall of partially or totally circular cross-section or of parabolic cross-section.

These examples of ancillary instruments are only embodiments of the invention which is not limited thereto. For example, the embodiments illustrated above have principally two ends 21, 22 (or 51, 52; 61, 62; 91, 92; 210, 220) of curved cross-section having substantially coaxial generatrices ($\Delta$).

Figure 18:
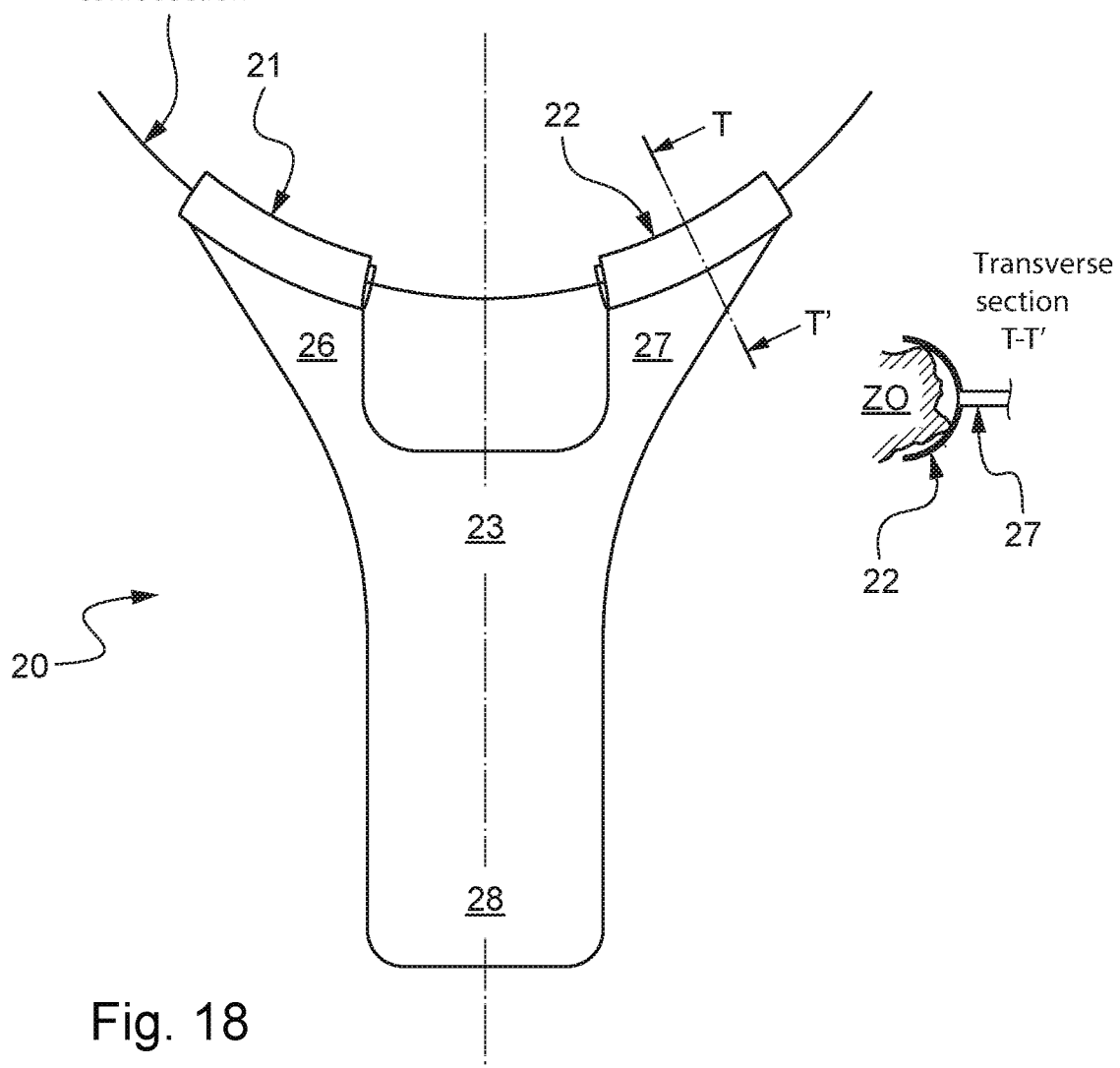

In a variant illustrated in FIG. 18, the two ends still have curved transverse cross-sections (convex or concave, according to the cross-section T-T'), but also have longitudinal cross-sections (cross-section along the plane of the ancillary instrument) which belong to the same conical curve, for example a circle of perpendicular axis formed by the plane of the Y-shaped ancillary instrument, an ellipse in that same plane, or for instance a parabola. This makes it possible to facilitate the rotation of the ancillary instrument in a plan containing the ancillary instrument. This ease of rotation may for example compensate for a defect in rocking/pivoting on account of undesirable contacts with the operating area ZO. This ease of rotation may also be used to attain the position in which the two planar surfaces 231, 232 of the third contact part 230 (see the embodiments of FIG. 8) are placed in contact with the operating area at the points R3 and R3'.

FIG. 9 shows an operating theatre ZS equipped with a surgical orientation system. By way of example, a system SYS1' is shown here, comprising an ancillary instrument 20' and a tool 30' equipped with the "MEMS" determining means and wireless communicating means.

The operating theatre ZS is equipped with a device 110 for displaying images and for data processing, such as a computer. The device 110 comprises a screen 111, a processor 112, means for entering and manipulating data 113 (a keyboard, a mouse, a voice sensor, a tactile surface, etc.), and means 114 for receiving the data communicated by the ancillary instrument 20' and/or the tool 30'.

The operating theatre comprises moreover an "operating entity" 100 comprising a surgeon 101 who operates on a patient 102 lying on an operating table 103.

The screen 111 makes it possible to display the images I obtained from the operating area ZO during the preoperative phase. The personnel of the operating suite, and particularly the surgeon, can consult the images during the operation. These images can be "static" or advantageously "dynamic". By "dynamic", it is meant that the reference frames of the ancillary instrument 20' and/or of the surgical tool 30' are determined, communicated to the computer 110, and displayed on the screen 111 in real time. The surgeon 101 can then have a precise idea of the orientation of his or her tools with respect to the vertebra.

In an embodiment, the system is interactive and allows the surgeon 101 to give oral instructions, for example "Display vertebra L5" so that the computer displays the image corresponding to vertebra L5.

FIG. 10 shows a flow chart of a preoperative phase P1, and FIG. 11 shows a flow chart of a perioperative phase P2.

Phase P1 comprises the steps S1 to S5. In step S1, at least one image I of at least one operating area ZO is taken, for example by tomodensitometry means. In step S2, at least three reference areas Z1, Z2, Z3 are determined or indicated by an operator and recorded in the case of a dynamic system, or simply noted in the case of a static system. At least one of the areas Z1 and Z2 is defined with the aid of two reference points R1, R1' or R2, R2' for which a contact with the ancillary instrument 20' is sought.

In the case of FIGS. 2 to 7, two pairs of two reference points (R1, R1') and (R1, R1') are determined, and a single reference point R3 is determined for the reference area Z3 located on the spinous process 5 in these examples.

In the case of FIGS. 8A and 8B, three pairs of two reference points (R1, R1'), (R2, R2') and (R3, R3') are determined.

These multiple reference points are determined by the computer 110, in particular as being protruding or protuberant points on the reference areas indicated, with which the ancillary instrument 20' will come into contact. For example, given the geometric dimensions of a chosen ancillary instrument, the computer 110 is able to determine which of a set of protruding points will come into contact with the ancillary instrument. The ancillary instrument is in particular chosen to satisfy the conditions of radius of curvature referred to earlier, it being understood that the radius of curvature of the reference areas aimed at may be estimated by modeling and approximation of the surface (concave or convex) of these reference areas.

In step S3, an orientation reference frame RO, as described above in relation to FIG. 4, is calculated by means of the reference points and then recorded or noted. In step S4, at least one directing vector [V]ro is determined for the surgical movement to be performed and then recorded or noted. In step S5, the process is repeated if necessary for other operating areas.

Phase P2 comprises the steps S11 to S16. In step S11, the operating area ZO is exposed. At step S12, a contact part 21' of the ancillary instrument 20' is placed in contact with the corresponding reference area Z1, for example in contact with two reference points R1, R1'. This may be a matter of engaging the convex contact part in the corresponding concave reference area (as in the right part of FIG. 3B with a cylinder), or of engaging the concave contact part on the corresponding convex reference area (that is to say of enveloping the convex reference area as shown in the left part of FIG. 3B with a channel).

At step S13, the other contact part 22' of the ancillary instrument 20' is placed in contact with the second reference area Z2, in identical manner to the first contact part if they are all concave and/or convex.

At this stage, the ancillary instrument 20' is engaged, by the two contact parts 21', 22', on the operating area. The three or four contact points R1, R1', R2, R2' may thus serve for rotational guiding of the ancillary instrument. Advantageously, these four contact points are placed in tangential contact with the concave or convex cylinder (depending on the ancillary instrument used) which thus determines a rotational axis).

At step S14, the ancillary instrument 20' is rotationally rocked, while maintaining the contacts R1, R1', R2, R2' without great effort by the operator. The third contact part 230 of the ancillary instrument 20' is then placed in contact with the third reference area Z3, for example simply laid on the reference point R3 (Examples of FIGS. 2 to 7), or placed in contact with the two reference points R3, R3' (Examples of FIGS. 8A and 8B).

In step S15, the orientation reference frame RO of the operating area ZO is determined and communicated, allowing calculation of the rotation matrix Mrors and the directing vector [V]rs using equation 1. Thus, the ancillary instrument according to the invention makes it possible to determine simply and rapidly the orientation of the operating area, for example a vertebra, for the purposes of performing an act, for example a surgical act.

In step S16, the surgical tool is used for performing a surgical movement according to the calculated directing vector.

FIG. 12 shows a non-transitory medium 120 which can be read by a computer and which comprises a program 121 of computer-executable instructions. The program of instructions can comprise the calculation algorithm described in relation to FIG. 4.

Embodiments moreover relate to an assembly or "kit" of at least two ancillary instruments 20, 20', 50, 60, 90, 200, each ancillary instrument being designed for operating areas ZO that are different from one another, for example having different dimensions, different angles between the branches, different first and second contact parts, different third contact parts etc. This allows a range of anatomical variations to be covered. In one embodiment, the ancillary instruments 20, 20', 50, 60, 90, 200 have different sizes, for example small, medium, and large.

It will be understood by a person skilled in the art that the embodiments described above can be modified.

For example, the communication means 25, 35, 45, 55, 65 can be a digital screen, light-emitting diodes ("LEDs") for example green, orange and red which light up, wired connections (a cable connected to the surgical tool or to the data processing device), wireless connections (Wi-Fi, NFC, Bluetooth, etc.), an auditory signal and, more generally, any means for communicating information.

In the above, the contact areas 23, 53, 63, 93 have been described as substantially planar areas which are placed on a tangential contact area ZT. (By "substantially planar" is meant that the area is more or less planar within manufacturing limits). Nevertheless, it will be understood by a person skilled in the art that these contact areas can have any other shape designed for coming into contact with a determined area.

In an embodiment, not shown, a tool for determining and communicating an orientation reference frame is fixed on the operating area ZO itself in order to continuously verify its position, for example in order to ensure that the patient has not moved during the operation, for very delicate operations.

The position of the patient, and more particularly of the operating area, can be adjusted until the correct orientation is found. Means (straps, clamps, etc.) for holding the operating area (the patient) in a given position can be utilized, either before the operation, or during the operation.

It will be understood by a person skilled in the art that certain elements described in relation to an embodiment (for example the determining and communicating means, the "MEMS", etc.) can be applied to other embodiments.

In particular, a convex contact part may be combined with a concave contact part (see for example FIG. 5) within the same ancillary instrument. Furthermore, a first contact part (concave or convex) may be combined with a second contact part which is able to perform a contact with the operating area at a single point. For example, the second contact part may be formed by a straight ridge (whether or not provided with non-slip spikes) or by a pointed member configured to come into contact with a single reference point of the second reference area Z2.

Furthermore, a convex part may be of any type: roll, roller, cylinder, sphere, semi-cylinder or partial cylinder (the cross-section is a part circle), or more generally any rounded form. A concave part may be of any type: channel with a cross-section that is partially circular or parabolic or V-shaped, spherical dome, end wall that is semi-cylindrical or partially cylindrical.

These convex/concave terminal parts of the branches of the Y-shaped ancillary instrument may be fixedly secured to the branches or be rotatably mounted.

The axes of revolution of the convex/concave parts (the rotational axes as the case may be) may be coaxial or offset or possibly even inclined relative to each other (that is to say not parallel), according to the anatomy of the operating area.

The surgical tool is for example a perforator, a screwdriver and, in general, any tool that allows a surgical procedure to be performed.

The materials used for the ancillary instrument and the surgical tool can, preferably, be sterilized and pose no biocompatibility problem.

As mentioned above, in certain embodiments, it is not obligatory that the surgical tool is equipped with means for determining and communicating orientation. In certain cases, once the orientation reference frame RO has been obtained, the surgeon can easily determine himself the correct angle, for example an angle of 90° with respect to the orientation reference frame of the ancillary instrument.

In certain embodiments, the branches of the ancillary instrument 20, 20', 50 60, 90, 200 can be articulated about the central area, for example by means of hinges arranged between the central area and each branch.

Finally, other methods of calculating the directing vectors can be implemented.

Figure 13A:
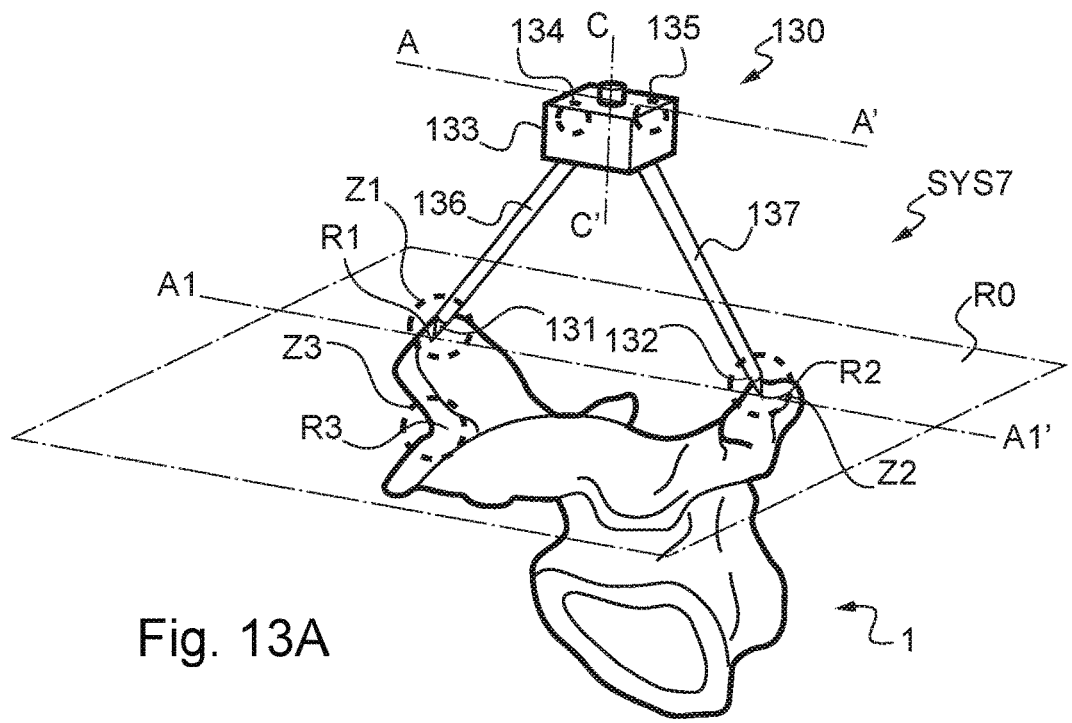
FIGS. 13A and 13B show perspective views of a simplified orientation system according to another embodiment, in two different measuring positions.
Figure 13B:
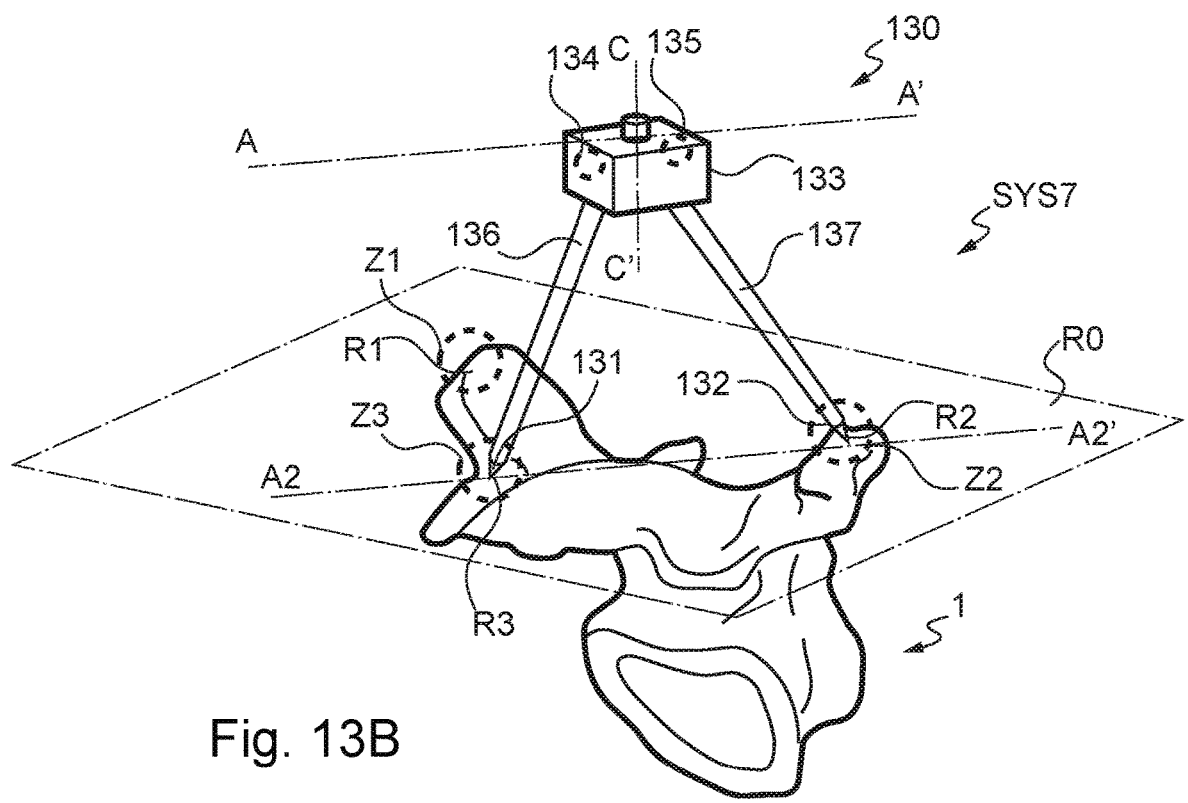

FIGS. 13A and 13B show perspective views of a simplified orientation system SYS7 according to another embodiment, in two different measuring positions.

The system SYS7 comprises an ancillary surgical instrument 130 and a tool (not shown for reasons of simplicity). The ancillary instrument 130 is in the form of a compass with two branches. It comprises: a first branch 136 having a first contact terminal end 131 configured to come into contact with a first reference area Z1 of an operating area 1; a second branch 137 having a second contact terminal end 132 configured to come into contact with a second reference area Z2 of the operating area 1; a fixed part or "housing" 133 relative to which the two branches 136, 137 move to open or close the ancillary instrument 130, such that, on opening or closing the ancillary instrument, the first and second terminal ends 131, 132 form an axis (A1-A1') which is constantly parallel to a reference axis (A-A') of the fixed part 133. The housing 133 may serve as a grip means (or handle) in order for an operator to be able to manipulate the ancillary instrument.

The ancillary instrument 130 further comprises a means 134 for determining an orientation of the ancillary instrument in a Galilean reference frame and, optionally, a means 135 for communicating orientations so determined by the means 134 (not shown in detail). As explained below, the means for determining an orientation 134 may be included in a means for determining a reference frame RA for orientation or operation (and thus RO) in a Galilean reference frame. In this case, the communicating means 135 is better able to communicate the orientation reference frame so determined.

These means 134, 135 may possibly be provided to be removable as in FIG. 6.

In this embodiment, the determining means 134 is a "MEMS" or "microelectromechanical system", of inertial measurement unit type, which determines the orientation of the axis (A1-A1') in the Galilean reference frame. This means can comprise a tri-axial accelerometer, a tri-axial gyroscope, and/or a tri-axial magnetometer, as known to a person skilled in the art and will thus not be explained in more detail. The communicating means 135 is a wired (cable) or wireless (contactless) connection, for example by Wi-Fi or Bluetooth, to transmit that orientation to a remote calculating system.

In the embodiment illustrated here, the first and second branches 136, 137 of substantially equal dimensions are rotatably mounted on the fixed part 133 and are arranged to open or close symmetrically relative to the fixed part 133. Thus, the spacing apart of the branches 136, 137 of the ancillary instrument may be adjusted according to the spacing apart of the reference areas Z1, Z2, to adapt, with a single ancillary instrument, to the highly variable dimensions of several operating areas.

Still in this embodiment, the inertial measurement unit 134 and optional transmitting means 135 are fixedly mounted on the fixed part 133. Thus, the orientation (A1-A1') to determine is the same as the orientation (A-A') of the inertial measurement unit 134 (and of the housing 133). A single determining means 134 (for example a single inertial measurement unit) is thus sufficient.

In the Figure, three reference areas Z1, Z2, Z3 are defined which each comprise a single reference point. The three points R1, R2, R3 are not aligned. The terminal ends 131, 132 of the branches 136, 137 of the ancillary instrument 130 are formed by points configured to come into contact with each of the reference points R1, R2, R3.

Of course, in a variant, one or other of the two ends 131, 132 (or even both) may be formed by a concave or convex end configured to come into contact with at least two reference points of the first or second corresponding reference area which is of convex or concave shape respectively. This may be any one of the configurations disclosed above in connection with FIGS. 1 to 12.

The ancillary instrument 130 may be used in a simple manner to determine in situ an operation reference frame of an operating area, in a Galilean orientation reference frame.

For this, two measurements are made as shown in FIGS. 13A and 13B, by successively positioning the two terminal ends 131, 132 of the ancillary instrument on each of two pairs of reference areas (Z1 and Z2 in FIG. 13A, and Z2 and Z3 in FIG. 13B). The determining means 134 thus obtains at least two orientations that are not parallel in the Galilean orientation reference frame: (A1-A1') at the time of the measurement in FIG. 13A and (A2-A2') at the time of the measurement in FIG. 13B.

These two orientations, by themselves, make it possible to determine the orientation or operation reference frame of the operating area 1, in the Galilean reference frame.

The first measured axis (A1-A1') may be used as first axis of the operation reference frame, and a unit vector can be associated with it. The vector product of this unit vector with the vector carried by the measured second axis (A2-A2') then makes it possible to define a second axis of the operation reference frame. A unit vector may also be associated with it. The vector product of the two unit vectors makes it possible to define the third axis of the operation reference frame, in the Galilean orientation reference frame. A unit vector is also associated with it. Thus, a reference frame is obtained that is made orthonormal.

These operations may be carried out in the determining means 134 or in a remote calculating system to which the orientations (A1-A1') and (A2-A2') will have been transmitted by the communicating means 135.

Figure 14A:
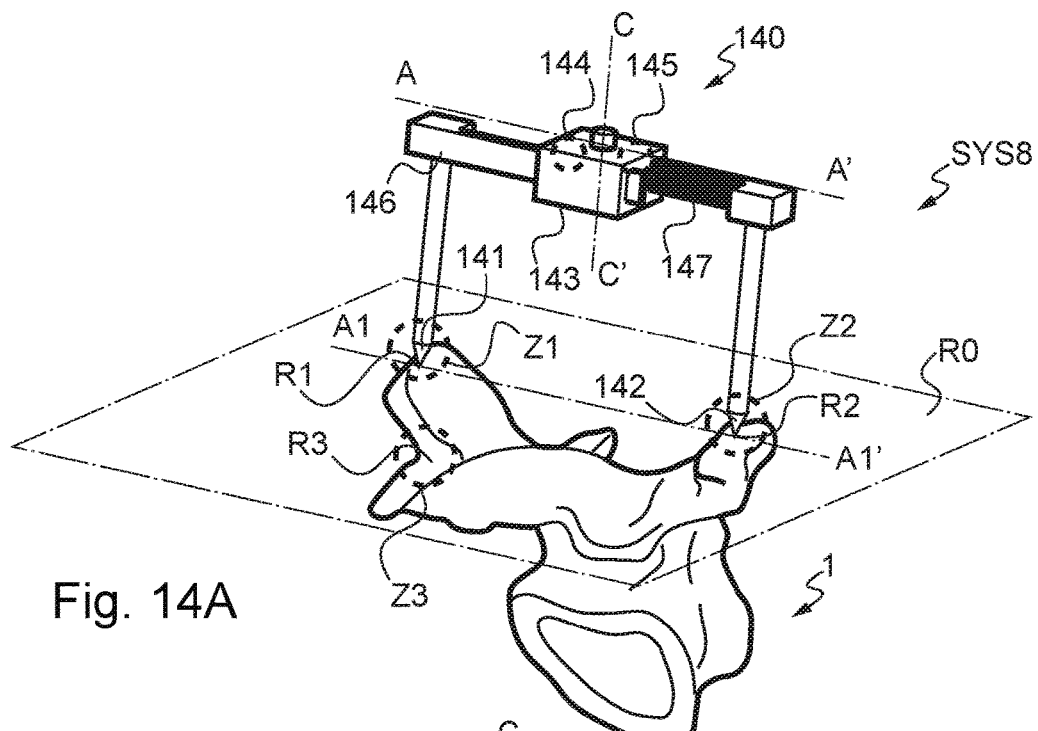
FIGS. 14A and 14B show perspective views of a variant simplified orientation system, in two different measuring positions.
Figure 14B:
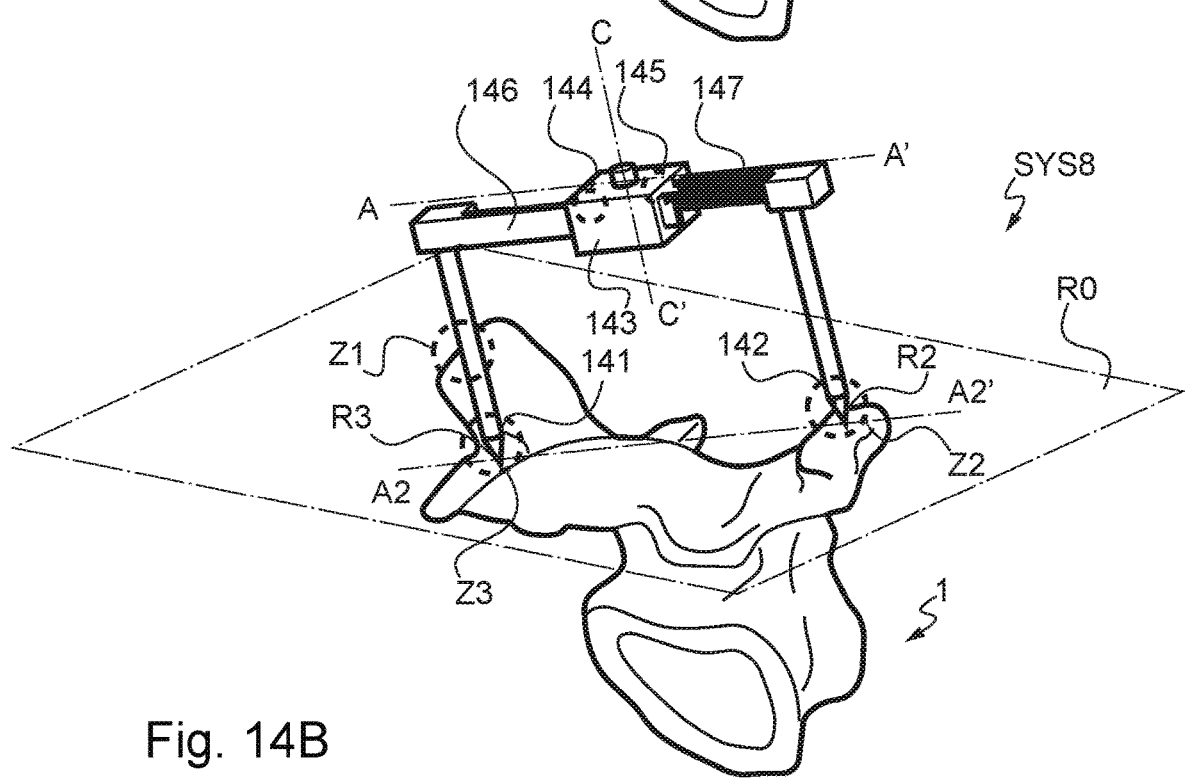
Figure 14C:
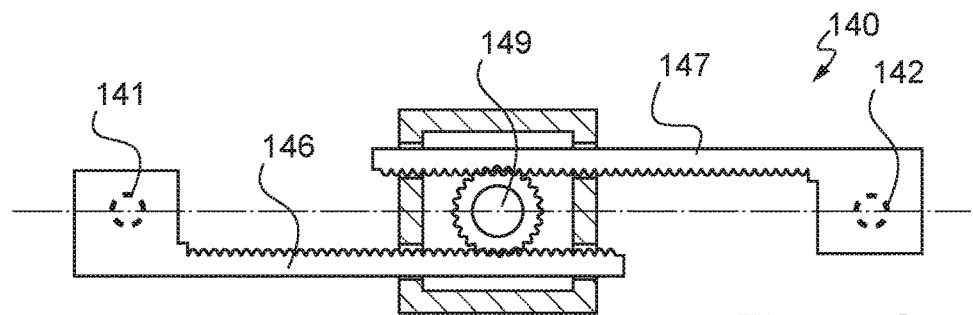
FIG. 14C shows a top view of the system of FIGS. 14A and 14B.

FIGS. 14A and 14B show perspective views of a simplified orientation system SYS8 according to another embodiment, in two different measuring positions. FIG. 14C shows a top view of the system SYS8.

The system SYS8 comprises an ancillary surgical instrument 140 and a tool (not shown for reasons of simplicity).

In the manner of ancillary instrument 130, the ancillary instrument 140 is in the form of a compass with two branches 146, 147, and comprises two terminal contact ends 141, 142 configured to come into contact with the reference areas Z1, Z2, Z3; a fixed part or "housing" 143 relative to which the two branches 146, 147 move to open or close the ancillary instrument 140, such that, on opening or closing the ancillary instrument, the first and second terminal ends 141, 142 form an axis (A1-A1') which is constantly parallel to a reference axis (A-A') of the fixed part 143. The ancillary instrument 140 further comprises a means 144 for determining an orientation of the ancillary instrument in a Galilean reference frame (possibly within a means for determining an orientation or operation reference frame RA), of inertial measurement unit type described above. The ancillary instrument 140 optionally comprises a means 145 for communicating the orientations determined (not shown in detail). These means 134, 135 may possibly be provided to be removable as in FIG. 6.

The ancillary instrument 140 is distinguished from the ancillary instrument 130 in that the first and second branches 146, 147 are mounted to be translatable relative to the fixed part and are arranged to slide in translation, possibly symmetrically, relative to the fixed part 143. The movement in translation of the branches 136, 137 of the ancillary instrument may be adjusted according to the spacing apart of the reference areas Z1, Z2, to adapt, with a single ancillary instrument, to the highly variable dimensions of several operating areas.

In this embodiment, the lengths of the branches 146, 147 may be adjusted along the axis A-A' using a pinion 149 which engages in adjustment rails provided on the branches 146, 147 (FIG. 14C).

In this embodiment, the terminal ends 141, 142 are points. As a variant, the configurations shown above in FIGS. 1 to 12 may be used.

In the example of the Figure, the determining means 134 is of inertial measurement unit type fixedly mounted to the fixed part. As a variant, such an inertial measurement unit may be fixedly mounted to the first or second branch 146, 147.

The ancillary instrument 140 is used in similar manner to the ancillary instrument 130 to determine in situ an operation reference frame of an operating area, in a Galilean orientation reference frame. For this, the two terminal ends 141, 142 of the ancillary instrument 140 are positioned successively on each of the two pairs of reference areas (Z1 and Z2 in FIG. 14A, and Z2 and Z3 in FIG. 14B), making it possible to obtain the two non-parallel orientations (A1-A1') and (A2-A2').

The simplified orientation systems SYS7 and SYS8 may first of all be used for surgical operations, according to a process rather similar to that of FIGS. 10 and 11. They may also be used to operate with precision on mechanical parts, outside a surgical context, for example to bore a part or screw a member into a part along a precise axis (sometimes with a desired orientation along a second axis).

A method of guiding for an operation on an operating area then comprises a prior phase directed to obtaining at least three reference areas in the operating area; to obtaining an operation reference frame by means of the reference areas; and to determining at least one operation axis (or even two) in the operation reference frame, for an operating movement to perform. This process is illustrated by FIGS. 15 and 16.

Figures 15, 16:
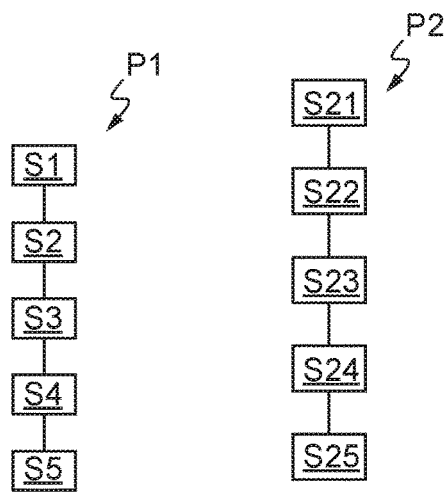
FIG. 15 shows a flowchart of a phase prior to an operation on an operating area.
FIG. 16 shows a flow chart of an active operating phase.

This prior phase P1 illustrated in FIG. 15 may be similar to that of FIG. 10, consisting of obtaining, by any means, three-dimensional modeling of the part on which to carry out the operation (step S1). Three reference areas Z1, Z2, Z3, preferably three reference points R1, R2, R3, are then determined, for example by an operator (step S2). The operation reference frame is then computed from the three reference points (step S3), then at least one directing vector [V]ro (or even two) is determined for the operation movement to perform (step S4). In step S5, the process is repeated if necessary for other operating areas.

Further to the prior phase, the operation consists of determining in situ the operation reference frame of the operating area in a Galilean orientation reference frame in which the operator is located, then of performing the operating movement on the operating area.

In a rather similar manner to FIG. 11, this operating phase P2 illustrated in FIG. 16 may comprise the access to the operating area (step S21).

Next, the ancillary instrument 130, 140 is laid on the operating area 1 for a first measurement. The ends 131, 132, 141, 142 are laid on the reference areas Z1, Z2. An axis (A1-A1') is formed between the two ends. If necessary, the distance between the ends 141, 142 is modified by the pinion 149 or the distance between the ends 131, 132 is modified by opening/closing the compass 130. This measuring position is illustrated in FIGS. 13A and 14A.

After stabilization of the ancillary instrument, a measurement of the orientation of the axis (A1-A1') is carried out by the inertial measurement unit 134, 144 (step S22). As a variant, a push-button (not shown) may be provided on the housing 133, 143 of the ancillary instrument to enable the operator to trigger the measurement on demand.

A first orientation of the operation reference frame is thus obtained.

Next, the ancillary instrument 130, 140 is moved on the operating area 1 for a second measurement. The ends 131, 132, 141, 142 are laid on another pair of reference areas, here Z2, Z3 (they could be two areas different from those used for the first measurement). An axis (A2-A2') is formed between the two ends. If necessary, the distance between the ends 141, 142 is modified by the pinion 149 or the distance between the ends 131, 132 is modified by opening/closing the compass 130. This measuring position is illustrated in FIGS. 13B and 14B.

After stabilization of the ancillary instrument or pressing on the push-button, a measurement of the orientation of the axis (A2-A2') is carried out by the inertial measurement unit 134, 144 (step S23). A second orientation, not parallel to the first, of the orientation reference frame is thus obtained.

Using these two measured orientations, the operation reference frame of the operating area is determined for example by the determining means 134, 144 and communicated to the outside of the ancillary instrument 130, 140 by the communicating means 135, 145 (step S24). This determination then makes it possible, using equation 1, to calculate the rotation matrix Mrors and the directing vector [V]rs of the movement to perform in the Galilean reference frame.

Once the operation reference frame in the Galilean reference frame has been determined and communicated, the operator carries out the planned operation movement on the operating area using an operating tool, for example he or she performs the boring of holes using the tool (step S25). The operating tool may be of the type of that shown in FIG. 2A or 6.

For this, the axis O-O' (not shown) of the operating tool in the Galilean orientation reference frame is placed in correspondence with the operating axis in the operation reference frame, for example by conversion of at least one of said axes of one reference frame to the other (for example with the aforementioned rotation matrix).

Preferably, the operating tool comprises determining means MEMS 34,84 and wired or wireless (contactless) communicating means 35,85, making it possible to determine an orientation (or axis) of the tool in real time in the Galilean orientation reference frame and to transmit it to the exterior. Thus, the operator can be guided efficiently to align his or her tool with the predetermined operating axis.

Figure 17:
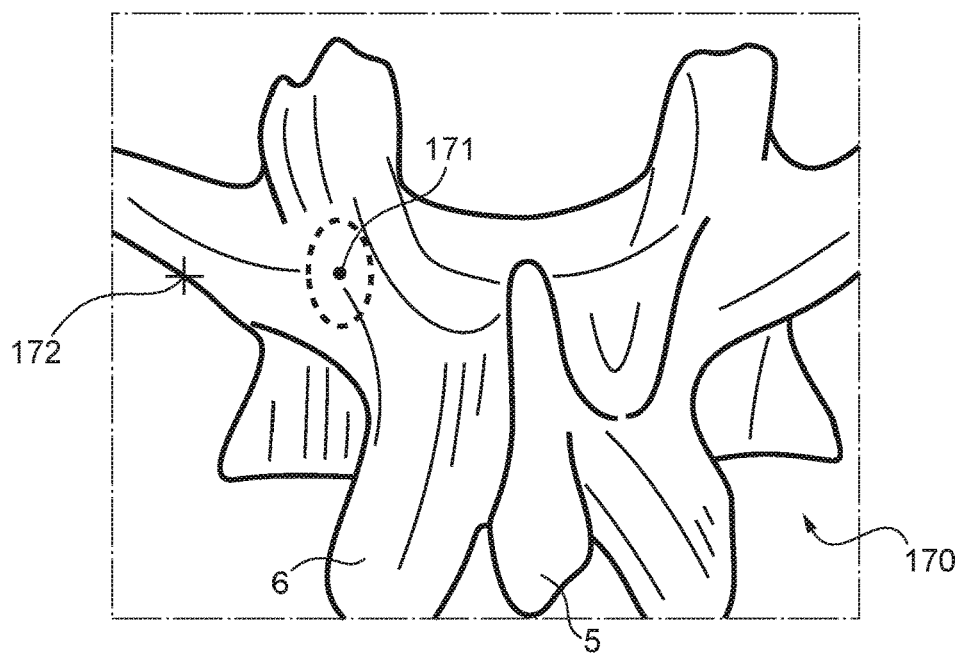
FIG. 17 illustrates a display for assisting the guiding of an operator in an operation.

For example, as illustrated in FIG. 17, a three-dimensional digital model 170 of the operating area 1 is displayed to the operator, on a screen 111 according to the operating axis. In other words, the displayed image corresponds to a view in a plane perpendicular to the operating axis, such that an operating point and the operating axis coincide on the screen. Thus, an indicator 171 (for example a cross or a circle) of the operating point on the operating area and an orientation indicator 172, in the display reference frame, of the operating tool positioned on the operating point may be displayed on the screen. To obtain the indicator 172 of the tool orientation, an angular offset between the operating axis and the axis of the tool may be estimated, by comparing the two orientations associated in the same reference frame, for example the directing vector [V]rs to a directing vector of the axis O-O' in the Galilean reference frame. This angular offset may be proportionally expressed on the screen via a spatial offset of the orientation indicator 172 relative to the operating point 171, in the direction of offset taking into account the display reference frame.

On that basis, the operator seeks to adjust the inclination of his or her tool to make the two indicators coincide. Advantageously, the operator may place the end 32 of his or her tool 30 on the point 171 to more easily align the tool based on the desired operating axis (Vrs), by moving only the handle (33, 81) of the tool 30 or 70. Next, he or she performs the operating movement on the operating area when the two indicators 171, 172 coincide.

Of course, several operating axes may be provided, that define a more precise orientation of the tool in the operation reference frame. In this case, the display may provide two indicators representing the two desired operating axes, and two indicators representing corresponding axes of the tool. Thus, the operator manipulates his or her tool so as to match the two pairs of indicators.

Furthermore, although the ancillary instruments 130, 140 have been mainly described with a determining means 134, 144 of inertial measurement unit type, other means for determining one or more orientations of the ancillary instrument may be provided by way of variant. By way of example, the ancillary instrument of compass type may be equipped, in the manner of the embodiment of FIG. 5, with non-aligned optical markers configured to be sensed by a plurality of video cameras which film the operating room in real time, in order to identify the positions, and thus the orientations, of the ancillary instruments in the Galilean reference frame. For example, an optical marker may be carried by the housing 133, 143, and an optical marker may be provided on each of the branches 136,137 and 146,147, for example in an area neighboring the terminal ends 131, 132 and 141,142.

The ancillary instrument of compass type 130, 140 may be provided in a kit also comprising a Y-shaped ancillary instrument described above and an operating tool. Preferably, a removable part 60-2 comprising the means for determining the operation reference frame and the communicating means may be provided, which can be temporarily fixed on request on one of the ancillary instruments and the tool of the kit, in the manner of FIG. 6.

These examples are only embodiments of the invention which is not limited thereto.

The invention claimed is:

1. An ancillary surgical instrument (20; 20'; 50; 60; 90; 200) comprising at least:
    a first contact part (21; 51; 61; 91; 210) configured to come into contact with a first reference area (Z1) of an operating area (ZO);
    a second contact part (22; 52; 62; 92; 220) configured to come into contact with a second reference area (Z2) of the operating area;
    a third contact part (23; 53; 63; 93; 230) configured to come into contact with a third reference area (Z3; R3) of the operating area; and
    a means (24; 54A, 54B, 54C; 84; 94) for determining an orientation reference frame (RA) of the ancillary instrument in a Galilean orientation reference frame (RS),
    wherein at least one of the first and second contact parts comprises a concave or convex end configured to come into contact with at least two reference points (R1; R1';

R2; R2') in the first or second corresponding reference area (Z1; Z2) which is of convex or concave shape respectively.

2. The ancillary instrument (20; 20'; 50; 60; 90; 200) according to claim 1, wherein the first and second contact parts each comprise a concave or convex end configured to come into contact with at least two reference points of the corresponding convex or concave reference area.

3. The ancillary instrument (20; 20'; 50; 60; 90; 200) according to claim 2, wherein the two ends are of curved cross-section with substantially coaxial generatrices (Δ).

4. The ancillary instrument (20; 20'; 50; 60; 90; 200) according to claim 3, wherein the convex end comprises a member in the form of a roll, roller, cylinder or sphere configured to engage in the corresponding concave reference area, or the concave end comprises a channel-shaped member or spherical dome, configured to engage on the corresponding convex reference area.

5. The ancillary instrument (20; 20'; 50; 60; 90; 200) according to claim 3, wherein the third contact part (23; 53; 63; 93; 230) is configured to come into contact with the third reference area (Z3) by rocking of the ancillary instrument while the first and second contact parts are in contact with the first and second reference areas respectively.

6. The ancillary instrument (20; 20'; 50; 60; 90; 200) according to claim 2, wherein the two ends have curved cross-sections and have longitudinal cross-sections which belong to the same conic section.

7. The ancillary instrument (20; 20'; 50; 60; 90; 200) according to claim 6, wherein the convex end comprises a member in the form of a roll, roller, cylinder or sphere configured to engage in the corresponding concave reference area, or the concave end comprises a channel-shaped member or spherical dome, configured to engage on the corresponding convex reference area.

8. The ancillary instrument (20; 20'; 50; 60; 90; 200) according to claim 6, wherein the third contact part (23; 53; 63; 93; 230) is configured to come into contact with the third reference area (Z3) by rocking of the ancillary instrument while the first and second contact parts are in contact with the first and second reference areas respectively.

9. The ancillary instrument (20; 20'; 50; 60; 90; 200) according to claim 2, wherein the convex end comprises a member in the form of a roll, roller, cylinder or sphere configured to engage in the corresponding concave reference area, or the concave end comprises a channel-shaped member or spherical dome, configured to engage on the corresponding convex reference area.

10. The ancillary instrument (20; 20'; 50; 60; 90; 200) according to claim 2, wherein the third contact part (23; 53; 63; 93; 230) is configured to come into contact with the third reference area (Z3) by rocking of the ancillary instrument while the first and second contact parts are in contact with the first and second reference areas respectively.

11. The ancillary instrument (20; 20'; 50; 60; 90; 200) according to claim 1, wherein the convex end comprises a member in the form of a roll, roller, cylinder or sphere configured to engage in the corresponding concave reference area, or the concave end comprises a channel-shaped member or spherical dome, configured to engage on the corresponding convex reference area.

12. The ancillary instrument (20; 20'; 50; 60; 90; 200) according to claim 11, wherein the member forming a convex or concave end is rotatably mounted on the ancillary instrument.

13. The ancillary instrument (20; 20'; 50; 60; 90; 200) according to claim 1, wherein the third contact part (23; 53; 63; 93; 230) is configured to come into contact with the third reference area (Z3) by rocking of the ancillary instrument while the first and second contact parts are in contact with the first and second reference areas respectively.

14. The ancillary instrument (20; 20'; 50; 60; 90; 200) according to claim 13, wherein the concave or convex end comprises a surface which has a curved cross-section around an axis of revolution, and the rocking takes place around the axis of revolution.

15. The ancillary instrument (20; 20'; 50; 60; 90; 200) according to claim 1, in the shape of a letter wye (Y) and comprising:
    at least two branches (26, 27; 56, 57; 66, 67; 96, 97; 260; 270) at the ends of which the first and second contact parts (21, 22; 51, 52; 61, 62; 91, 92; 260, 270) are disposed;
    a third branch (28; 58; 68; 98; 280) in the form of a handle; and
    a central area having a lower face which forms the third contact part (23; 53; 63; 93; 230).

16. An operating theatre (ZS) equipped with an ancillary surgical instrument (20, 20'; 50; 60; 90; 200) according to claim 1 and with a device (110) for displaying images and data processing comprising:
    a screen (111) for displaying images (I) taken of the operating area (ZO);
    a processor (112);
    means for entering and manipulating data (113); and
    means (114) for receiving data communicated by the ancillary instrument.

17. A surgical orientation system (SYS1, SYS1'; SYS2; SYS3; SYS4; SYS5; SYS6) comprising at least one ancillary instrument (20, 20'; 50; 60; 90; 200) according to claim 1 and a surgical tool (30; 70) comprising:
    means (34; 84) for determining an orientation reference frame (RT) of the tool; and
    means (35; 85) for communicating the orientation reference frame (RT) of the tool.

18. The system (SYS4) according to claim 17, wherein the ancillary instrument (60-1) and the surgical tool (70) are configured to be coupled to one and the same device (60-2) for determining and communicating an orientation reference frame (RA, RT).

19. A method (P1) for preoperative preparation of a surgical operation, comprising the steps consisting of:
    taking (S1) at least one three-dimensional image (I) of an operating area (ZO);
    determining (S2) at least two reference points (R1; R1') in a first reference area (Z1) of the operating area, and at least two other reference points (R2; R2') of a second reference area (Z2) of the operating area, from the three-dimensional image;
    calculating (S3) an orientation reference frame (RO) by means of the reference points, the orientation reference frame being subsequently identifiable by an ancillary instrument according to claim 1; and
    determining (S4) at least one local axis ([V]ro) in the reference frame, for a surgical movement to be performed.

20. A non-transitory computer-readable medium (110) on which is stored a program which, when executed by a computer, carries out the method according to claim 19.

* * * * *